United States Patent
Bonutti

[19]

[11] Patent Number: 6,045,551
[45] Date of Patent: Apr. 4, 2000

[54] BONE SUTURE

[76] Inventor: Peter M. Bonutti, 1303 W. Evergreen Plz., Effingham, Ill. 62401

[21] Appl. No.: 09/363,707

[22] Filed: Jul. 29, 1999

Related U.S. Application Data

[63] Continuation-in-part of application No. 09/323,488, Jun. 1, 1999, and a continuation of application No. 09/019,977, Feb. 6, 1998, Pat. No. 5,921,986.

[51] Int. Cl.[7] .................................................... A61B 17/56
[52] U.S. Cl. ................................ 606/60; 606/57; 606/215
[58] Field of Search ................................ 606/60, 72, 75, 606/215, 216, 232

[56] References Cited

U.S. PATENT DOCUMENTS

| | | | |
|---|---|---|---|
| 3,513,848 | 5/1970 | Winston et al. | 606/228 |
| 4,414,166 | 11/1983 | Charlson et al. . | |
| 4,456,005 | 6/1984 | Lichty | 606/60 |
| 4,506,681 | 3/1985 | Mundell . | |
| 4,645,503 | 2/1987 | Lin et al. . | |
| 4,662,063 | 5/1987 | Polonsky . | |
| 4,750,492 | 6/1988 | Jacobs . | |
| 4,792,336 | 12/1988 | Hlavacek et al. | 606/13 |
| 4,832,025 | 5/1989 | Coates | 606/232 |
| 4,935,028 | 6/1990 | Drews | 606/228 |
| 5,098,433 | 3/1992 | Freedland | 606/60 |
| 5,156,613 | 10/1992 | Sawyer . | |
| 5,163,960 | 11/1992 | Bonutti | 606/232 |
| 5,209,776 | 5/1993 | Bass et al. . | |
| 5,254,113 | 10/1993 | Wilk . | |
| 5,306,280 | 4/1994 | Bregen et al. . | |
| 5,370,646 | 12/1994 | Reese et al. | 606/72 |
| 5,474,554 | 12/1995 | Ku . | |
| 5,531,759 | 7/1996 | Kensey et al. | 606/232 |
| 5,593,422 | 1/1997 | Muijs Van De Moer et al. | 606/232 |
| 5,593,425 | 1/1997 | Bonutti et al. | 606/213 |
| 5,620,461 | 4/1997 | Muijs Van De Moer et al. | 606/213 |
| 5,810,884 | 9/1998 | Kim . | |

*Primary Examiner*—Gary Jackson
*Attorney, Agent, or Firm*—Tarolli, Sundheim, Covell, Tummino & Szabo L.L.P.

[57] ABSTRACT

An anchor connected with a suture is moved through a passage between opposite sides of a bone. The anchor is then pivoted to change its orientation. A second anchor is connected with the suture. While tension is maintained in the suture, the suture is secured against movement relative to the anchors. This may be done by tying the suture or by using a suture retainer to hold the suture. A suture retainer may be used in place of the second anchor. The passage may extend across a fracture in the bone. The passage may have either a nonlinear or linear configuration. A tubular member may be positioned in the passage with the tubular member extending into portions of the passage on opposite sides of the fracture. Opposite end portions of the tubular member may be disposed in a compact outer layer of the bone. If desired, a member other than a suture may be used as a force transmitting member between the two anchors. The tubular member may be formed of bone.

56 Claims, 7 Drawing Sheets

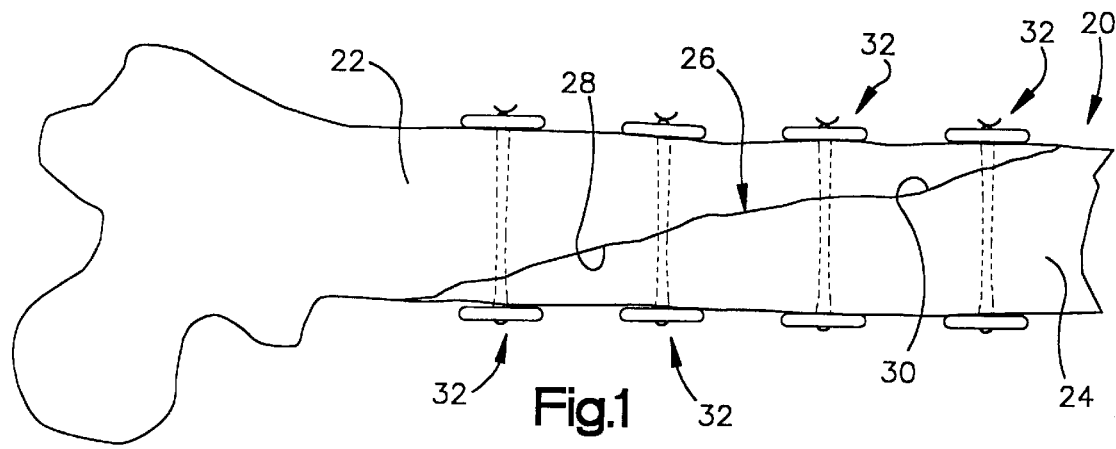
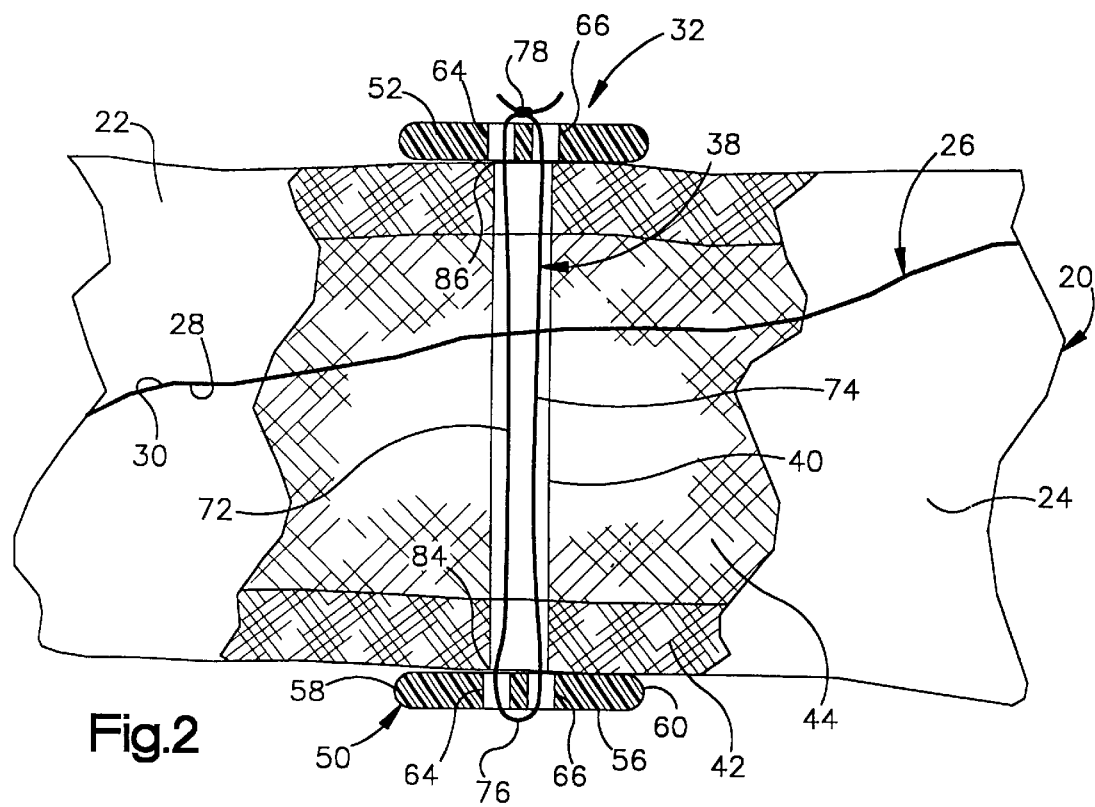

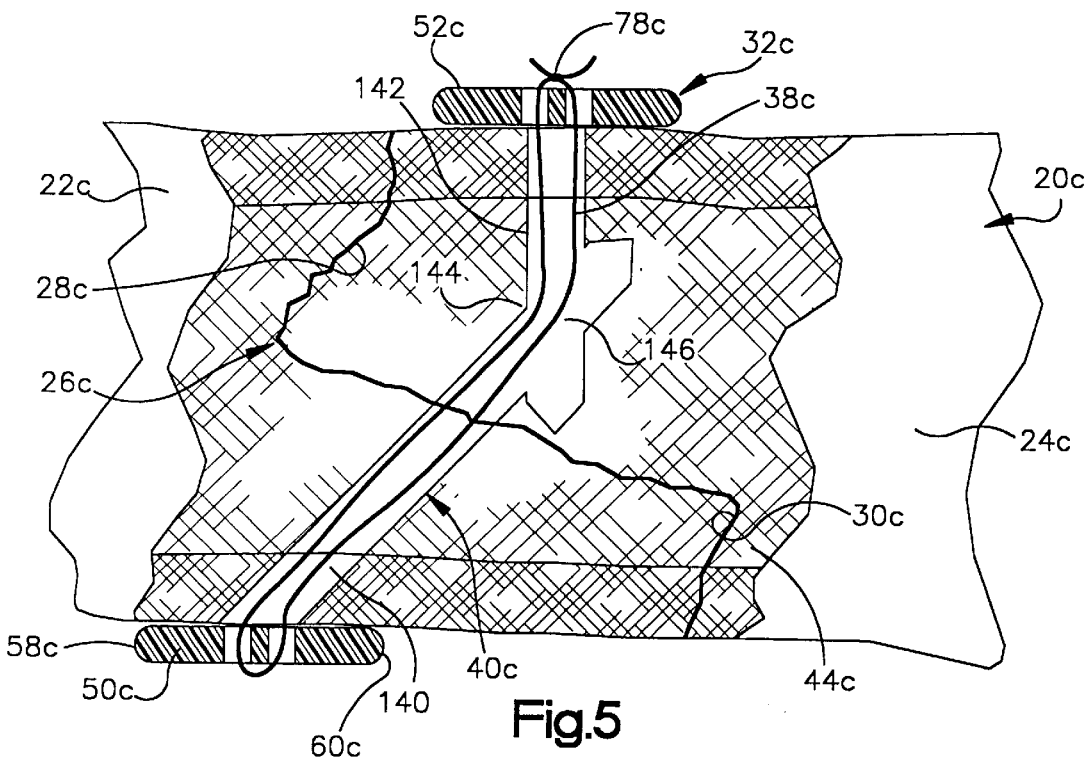
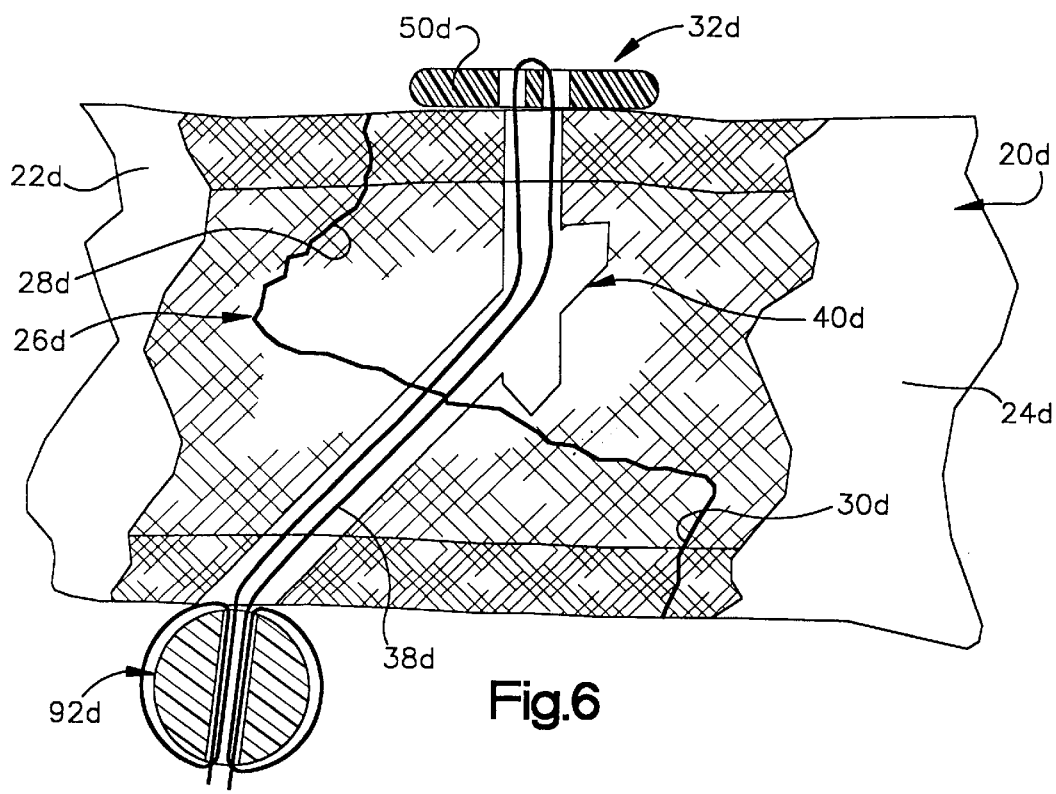

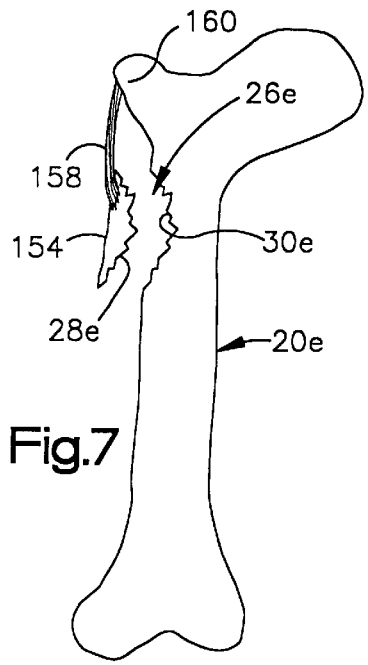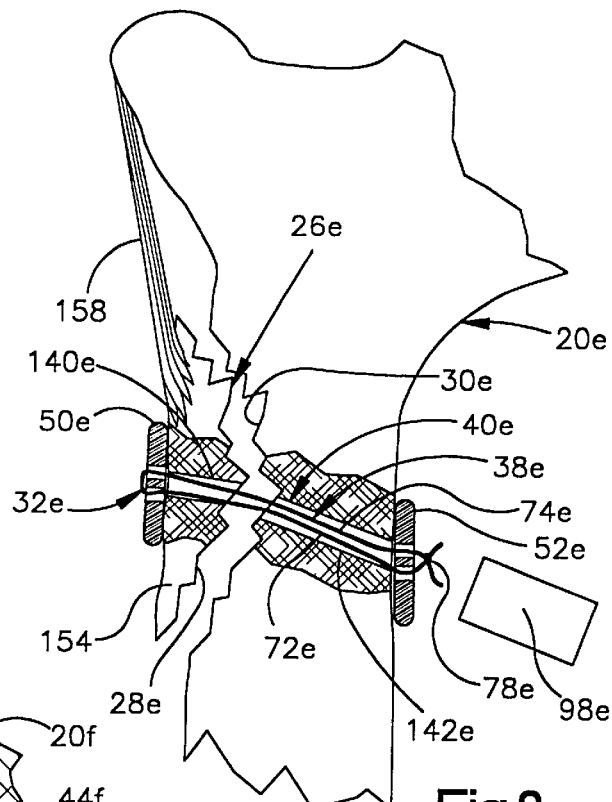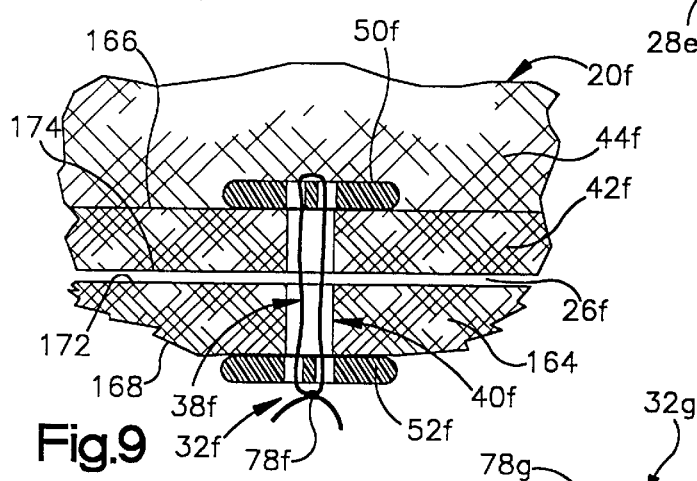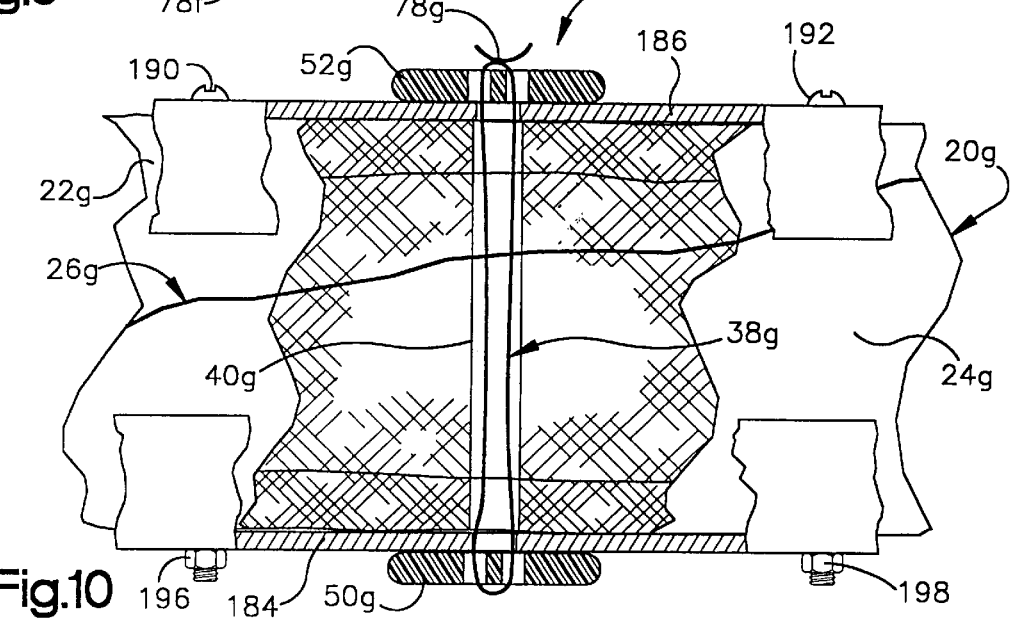

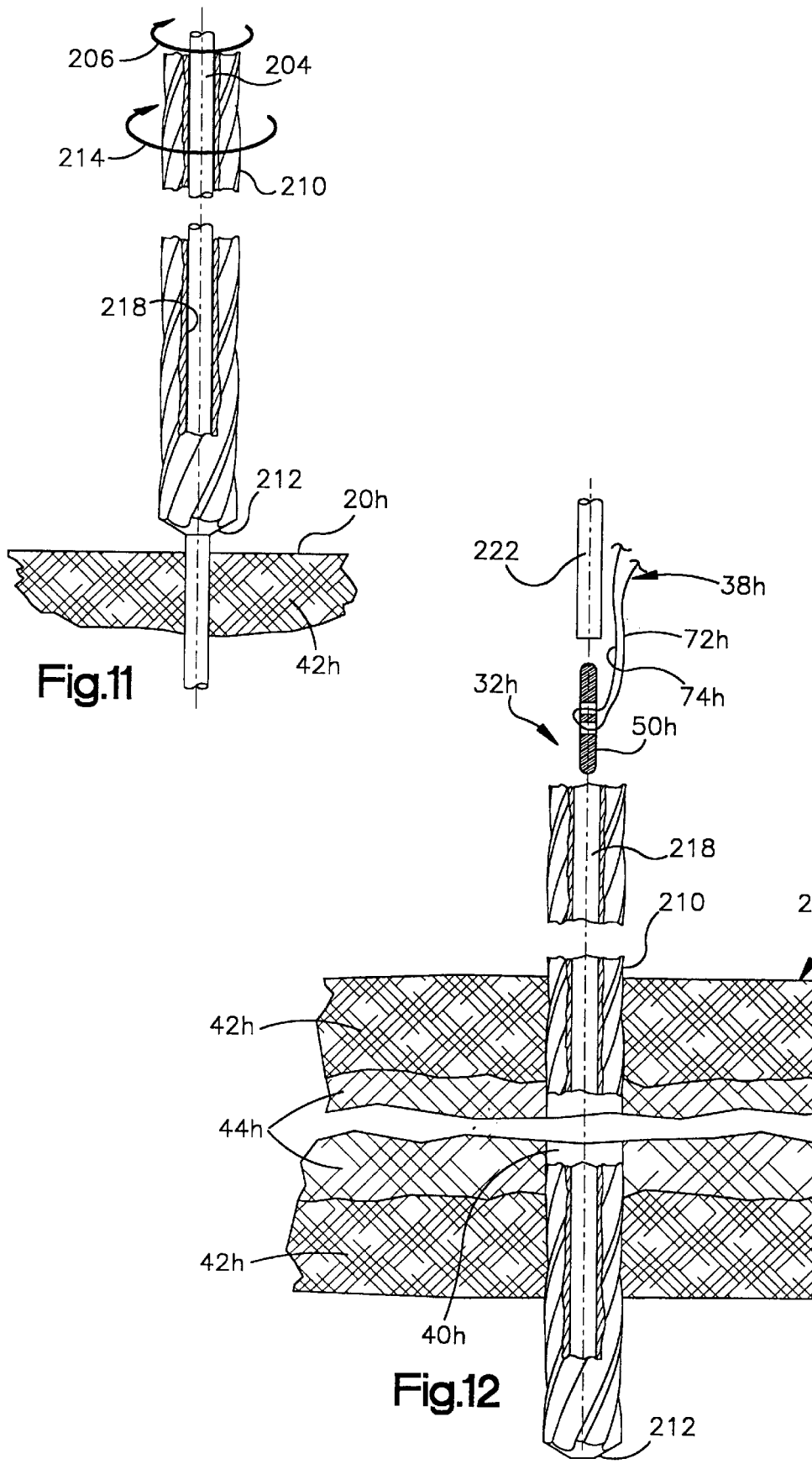

6,045,551

1

BONE SUTURE

RELATED APPLICATION

This application is a continuation-in-part of U.S. patent application Ser. No. 09/323,488, filed Jun. 1, 1999 by Peter M. Bonutti and entitled "Bone Suture". The aforementioned application Ser. No. 09/323,488 is itself a continuation of U.S. patent application Ser. No. 09/019,977 filed Feb. 6, 1998 by Peter M. Bonutti and entitled "Bone Suture" (now U.S. Pat. No. 5,921,986). The benefit of the earlier filing date of the aforementioned application Ser. Nos. 09/019,977 and 09/323,488 is claimed for all subject matter common to the aforementioned application Ser. Nos. 09/019,977 and 09/323,488 and this application.

BACKGROUND OF THE INVENTION

The present invention relates to a new and improved method and apparatus for securing sections of a fractured bone and/or securing body tissue to bone.

When a bone is broken or fractured, it is necessary to press sections of the bone on opposite sides of the fracture together in order to promote healing of the bone. Bone screws have been used with or without metal plates to hold the sections of the fractured bone against movement relative to each other. In addition, it has been suggested that avulsion fractures could be treated by using wire sutures between sections of bone in a matter similar to that disclosed in U.S. Pat. No. 5,474,554. It has also been suggested that an anchor could be retained in a bone is a manner disclosed in U.S. Pat. Nos. 5,527,343 and 5,534,012.

SUMMARY OF THE INVENTION

The present invention relates to a method of securing sections of a fractured bone. Sections of a fractured bone are held against movement relative to each other by a force transmitting member, such as a suture, which extends through a passage in the bone. The passage in the bone may have a linear or nonlinear configuration. Tension is maintained in the force transmitting member to press surfaces on the fracture together by securing anchors and/or retainers to opposite ends of the force transmitting member. It is believed that a suture may advantageously be used as the force transmitting member.

A tubular member is positioned in a linear or nonlinear passage through the bone. The tubular member extends into portions of the passage on opposite sides of the fracture. End portions of the tubular member may be positioned in a compact outer layer of the bone. The tubular member may be formed of bone. The force transmitting member may be formed of bone or other body tissue.

BRIEF DESCRIPTION OF THE DRAWINGS

The foregoing and other features of the invention will become more apparent upon a consideration of the following description taken in connection with the accompanying drawings wherein:

FIG. 1 is a schematic illustration of a bone having a fracture which has been treated with sutures and suture anchors;

FIG. 2 is an enlarged fragmentary schematic sectional view of a portion of the bone of FIG. 1 and illustrating the manner in which a suture extends across the fracture and interconnects suture anchors on opposite sides of the fracture;

Figure 3:
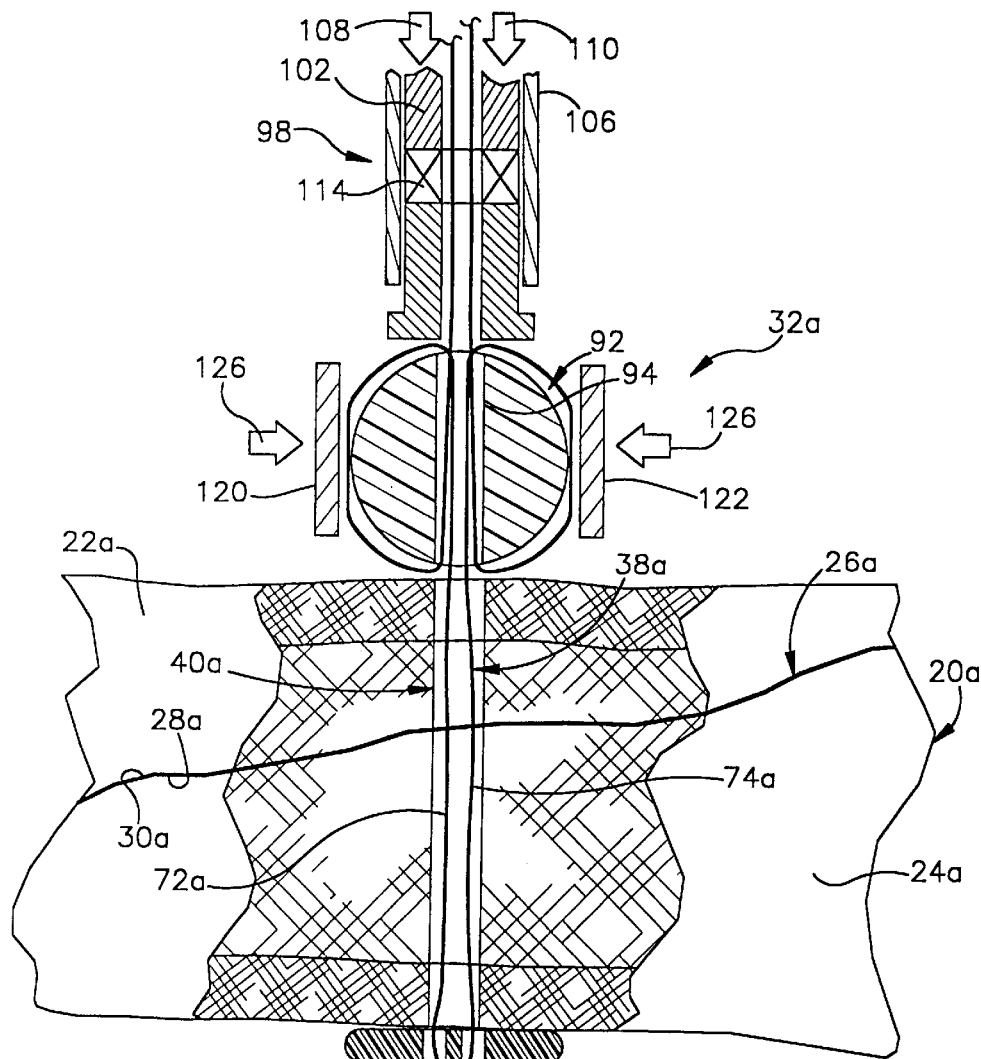
FIG. 3 is a schematic illustration, generally similar to FIG. 2, illustrating the manner in which a suture retainer is used
Figure 4:
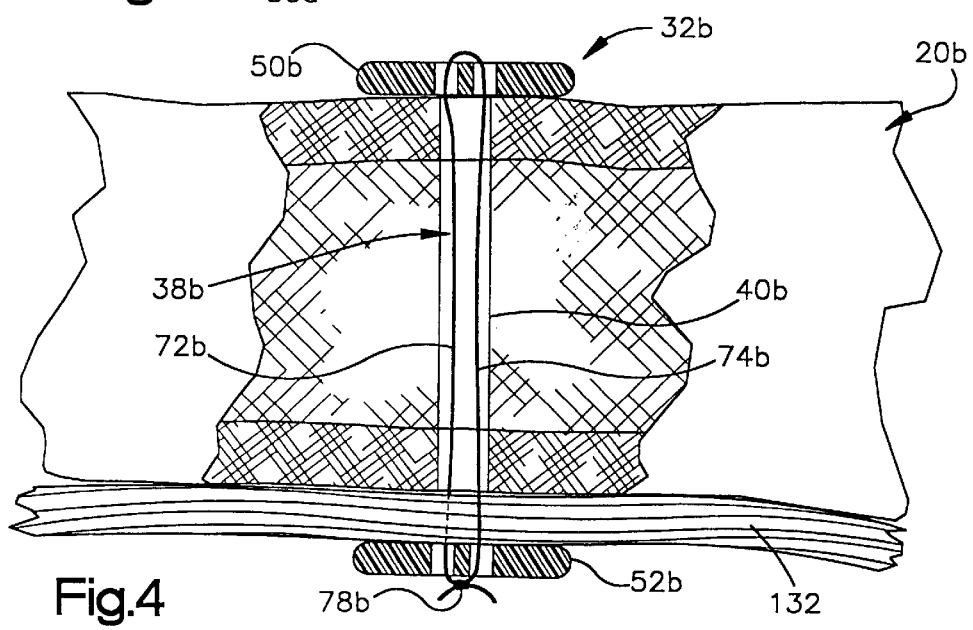
Figure 13:
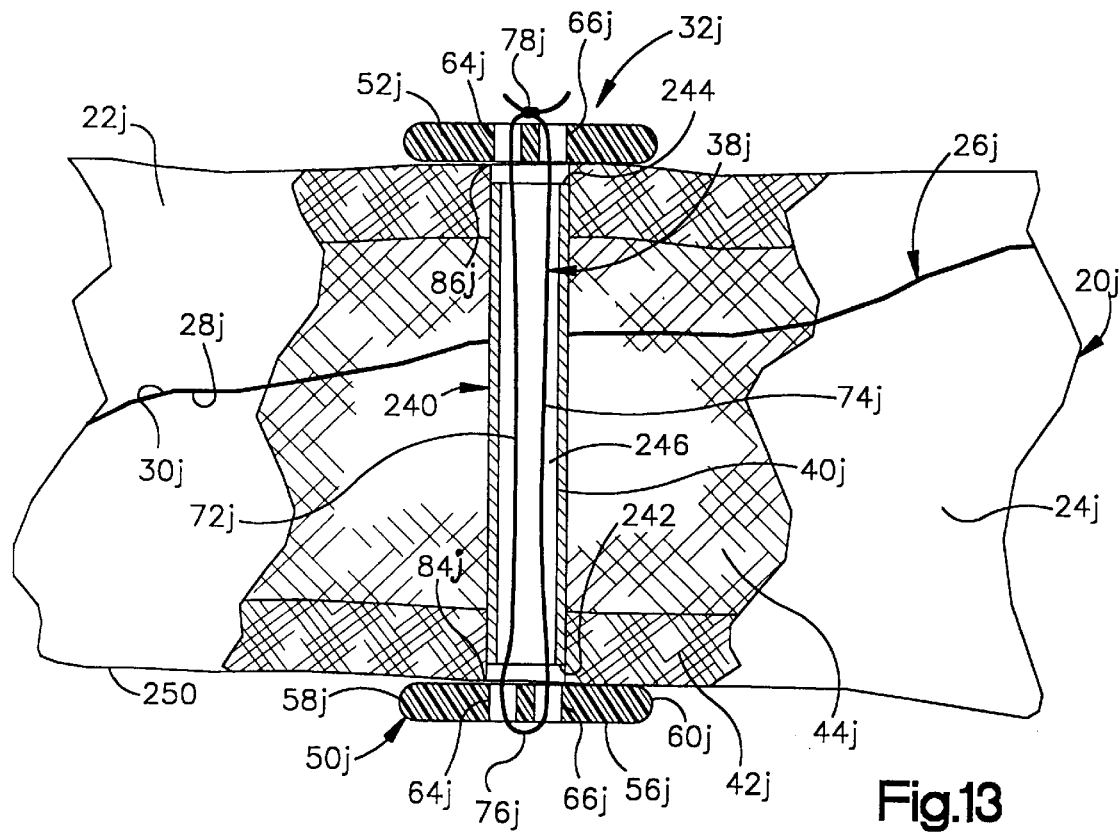
Figure 14:
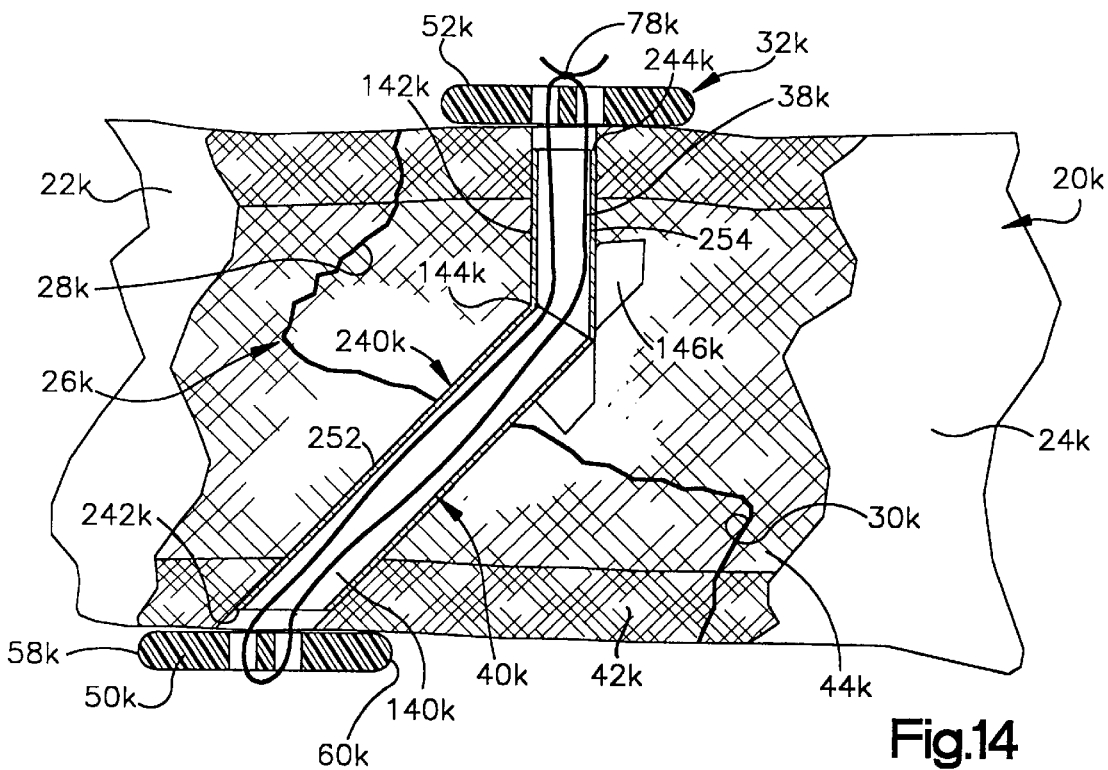
Figure 15:
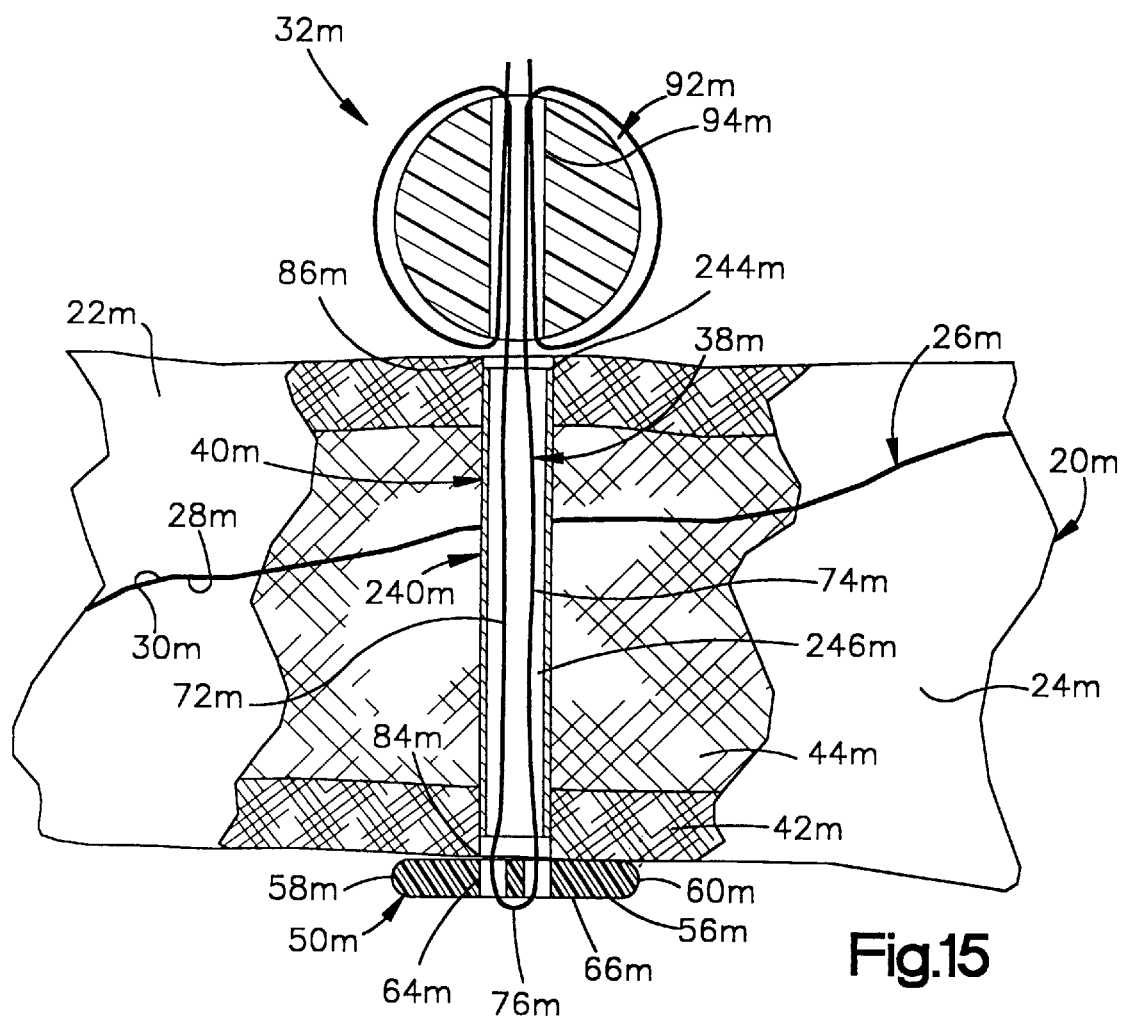

2 to maintain tension in a suture which extends across a fracture to a suture anchor;

FIG. 4 is a schematic illustration, generally similar to FIGS. 2 and 3, illustrating the manner in which body tissue is connected with a bone using a suture and suture anchors;

FIG. 5 is a schematic illustration, generally similar to FIGS. 2–4, illustrating the manner in which a suture extends between suture anchors through a nonlinear passage;

FIG. 6 is a schematic illustration, generally similar to FIG. 5, illustrating the manner in which a suture extends between a suture anchor and a suture retainer through a nonlinear passage;

FIG. 7 is a schematic illustration depicting a bone which has been fractured in such a manner as to have a bone fragment connected with the bone by muscle or other fibrous tissue;

FIG. 8 is a schematic illustration depicting the manner in which the bone fragment of FIG. 7 is connected to the bone by a suture and a pair of suture anchors;

FIG. 9 is a schematic illustration depicting the manner in which a bone fragment is connected with a bone by a suture which extends between an anchor within the bone and an anchor which engages the bone fragment;

FIG. 10 is a schematic illustration, generally similar to FIGS. 2–4 and illustrating in the manner in which plates and rigid fasteners are used in association with a suture and anchors to treat a bone fracture;

FIG. 11 is a schematic illustration depicting the manner in which a thin elongated member is moved through bone and the manner in which a drill is moved along the thin elongated member to enlarge a passage formed in the bone by the thin elongated member;

FIG. 12 is a schematic illustration depicting the manner in which an anchor is moved through a passage in the drill of FIG. 11 after the thin elongated member has been removed from the passage in the drill;

FIG. 13 is a schematic illustration, generally similar to FIG. 2, illustrating the manner in which a tubular member is positioned in a passage in the bone;

FIG. 14 is a schematic illustration, generally similar to FIG. 5, illustrating the manner in which tubular members are positioned in a nonlinear passage in a bone; and FIG. 15 is a schematic illustration, generally similar to FIG. 3, illustrating the manner in which a suture retainer is used with a tubular member which is positioned in a passage in a bone.

DESCRIPTION OF SPECIFIC PREFERRED EMBODIMENTS OF THE INVENTION

A bone 20 which has been fractured is illustrated in FIG. 1. The bone 20 is divided into two sections 22 and 24 by a fracture 26. Opposite side surfaces 28 and 30 of the fracture 26 are pressed together by bone suture assemblies 32.

It should be understood that the bone suture assemblies 32 may be utilized in the treatment of any one of many different types of fractures. The fractures may or may not result in the formation of one or more bone fragments. In FIG. 1, the bone suture assemblies 32 have been illustrated as interconnecting sections 22 and 24 of a complete bone fracture of the spiral type. However, the bone suture assemblies 32 could be utilized to connect a fragment of a bone to the main portion of the bone from which the fragment was broken off.

Each of the bone suture assemblies 32 has the same construction. However, the bone suture assemblies 32 could have different constructions if desired. The construction of one of the identical bone suture assemblies 32 is illustrated in FIG. 2.

The bone suture assembly 32 (FIG. 2) includes a flexible suture 38 which extends across the fracture 26. The suture 38 is disposed in a straight cylindrical passage 40 which extends diametrically across a generally cylindrical portion of the bone 20. The passage 40 extends through hard compact tissue of an outer layer 42 of the bone and through spongy or cancellous bone tissue 44 which is enclosed by the hard outer layer. Although the passage 40 has a linear configuration, the passage could have a nonlinear configuration if desired.

The suture 38 extends between a first suture anchor 50 disposed on one side of the fracture 26 and a second suture anchor 52 disposed on the opposite side of the fracture. Tension is maintained in the suture 38 to press the suture anchors 50 and 52 against opposite sides of the bone 20 with a predetermined force. This force presses the side surfaces 28 and 30 of the fracture 26 firmly together to promote healing of the fracture. If desired, buttons or other force distributing members could be provided between the anchors 50 and 52 and the bone 20. Body tissue could be disposed between the anchors 50 and 52 and the bone 20.

The suture 38 and/or suture anchors 50 and 52 may be formed of any desired natural or artificial material. For example, the suture 38 may formed of either a polymeric material or a metal. The suture 38 may be biodegradable. Any known suture material may be utilized to form the suture 38.

The suture anchors 50 and 52 have the same construction. However, the anchor 50 could have a construction which is different than the construction of the anchor 52. The anchor 50 has a cylindrical outer side surface 56 which extends between smooth rounded end portions 58 and 60. A pair of parallel cylindrical openings 64 and 66 extend diametrically through the anchor 50. The anchor 50 is free of sharp corners or projections to avoid cutting or abrading of body tissue disposed adjacent to the anchor.

The suture anchor 50 is made of a biocompatible material. Suitable materials include stainless steel or titanium, cobalt chrome and other biocompatible metals. Polymeric material may also be used, suitable polymeric materials includes polyethylene, polypropylene, and biodegradable material such as PLA and PGA. It is believed that it may be preferred to form the suture anchors 50 and 52 from biodegradable or bioerodible copolymers. If desired, the anchor 50 could be formed of body material or hydrophilic materials.

It is contemplated that the anchor 50 may have any desired configuration. For example, the anchor 50 could have any one of the configurations disclosed in U.S. Pat. No. 5,522,846 issued Jun. 4, 1996 and entitled "Suture Anchor". Alternatively, the suture anchor 50 could have the configuration disclosed in U.S. Pat. No. 5,534,012 issued Jul. 9, 1996 and entitled "Method and Apparatus for Anchoring a Suture".

Although the anchor 50 may have any desired configuration, the cross-sectional size of the anchor is such as to enable the anchor to be moved through the passage 40. In addition, the length of the anchor 50 is such as to enable it to span an opening at an end of the passage 40 and transmit force from the suture 38 to a substantial area on the outer layer 42 of the bone 20. It is believed that it will be preferred to form the anchor 50 in such a manner as to eliminate any sharp corners or projections.

In the illustrated embodiment of the invention, the anchor 50 has a cylindrical configuration. This particular anchor has an axial length of about two millimeters and a diameter of about one millimeter. The length of the anchor 50 may be approximately three times the diameter of the anchor. The openings 64 and 66 have a diameter of about one-half millimeter.

It should be understood that the foregoing dimensions have been set forth herein for purposes of clarity of description and it is contemplated that the size of the anchor 50 may vary as a function of the size of the bone being treated. Thus, relatively small anchors may be used in association with treatment of small bones in a wrist, hand, foot or ankle of a patient. Relatively large anchors may be used in association with treatment of larger bones in an arm, shoulder, leg or hip of a patient. It should be understood that the bone suture assembly 32 may be used in conjunction with many different bones other than the specific bones previously mentioned.

Only a single anchor 50 or 52 has been shown at opposite ends of the passage 40. It is contemplated that a plurality of anchors could be provided at each end of the passage 40. For example, a pair of separate or interconnected anchors could be provided in a manner similar to that disclosed in the aforementioned U.S. Pat. No. 5,534,012.

In the embodiment of the invention illustrated in FIG. 2, the suture 38 has a pair of limbs or sections 72 and 74 which extend through the openings 64 and 66 in the suture anchors 50 and 52. A connector section 76 interconnects the two limbs 72 and 74 of the suture 38 and engages a portion of the anchor 50. A knot 78 is formed in the opposite ends of the limbs 72 and 74 to interconnect the two limbs of the suture 38.

When the knot 78 is formed, a predetermined tension is present in the limbs 72 and 74 of the suture 38. This results in the suture anchors 50 and 52 being pressed firmly against the bone 20 with a predetermined force. This predetermined force is maintained during and after tying of the knot 78.

When the bone suture assembly 32 is to be used to treat the fracture 26 in the bone 20, the two sections 22 and 24 of the bone are pressed together at the fracture 26 to align the side surfaces 28 and 30 of the fracture. A drill is then used to form the passage 40 which extends diametrically through the generally cylindrical bone 20. Of course, the passage 40 could be formed by the use of a tool other than a drill. If desired, the passage 40 could have a noncircular cross-sectional configuration.

Once the passage 40 has been formed in the two sections 22 and 24 of the bone 20, a tubular cylindrical member is inserted into the passage 40 and extends diametrically through the bone 20. The leading end of the tubular cylindrical member is aligned with a circular outlet 84 from the passage 40. The opposite end of the tubular member is aligned with a circular inlet 86 to the passage 40. The tubular member has a thin cylindrical wall which engages the sections 22 and 24 of the bone 20. A cylindrical inner side surface of the tubular member defines a passage having a diameter which is only slightly less than the diameter of the passage 40.

By inserting the tubular member into the passage 40, the portions of the passage disposed on opposite sides of the fracture 26 are maintained in alignment. The tubular member may be flexible to enable the tubular member to be inserted into a nonlinear passage 40 through the bone 20. The tubular member may be formed of metal or a polymeric material. If the tubular member is formed of a polymeric material, it may be preferred to form the tubular member from a biodegradable or bioerodible copolymer.

The suture 38 is formed into a loop which extends through the openings 64 and 66 in the anchor 50. At this time, the suture 38 has a length which is substantially greater than the length illustrated in FIG. 2. The cylindrical anchor 50, with the suture 38 connected thereto, is then positioned in axial alignment with the tubular member which extends through the passage 40. Thus, the anchor 50 is moved to an orientation in which a longitudinal central axis of the anchor is coincident with the longitudinal central axis of the cylindrical passage in the tubular member which extends through the passage 40 in the bone 20.

The leading end 58 of the anchor 50 is then moved into the cylindrical tubular member which forms a liner for the passage 40. A pusher member pushes the anchor 50 from an upper (as viewed in FIG. 2) end of the tubular member along the passage 40 in the bone 20 and through the outlet 84 from the passage. As the anchor 50 moves through the passage 40, the suture 38 is pulled through the passage 40 by the anchor.

The orientation of the anchor 50 is then changed from an orientation in which the longitudinal central axis of the anchor 50 is aligned with the longitudinal central axis of the passage 40 to an orientation in which the longitudinal central axis of the anchor 50 extends generally perpendicular to the longitudinal central axis of the passage 40, i.e., the orientation shown in FIG. 2. To pivot the anchor 50 to the orientation shown in FIG. 2, as the anchor emerges from the outlet 84, the suture 38 is tensioned. The combination of the tension in the suture 38 and force applied against the trailing end 60 of the anchor by the pusher member causes the anchor to pivot about the trailing end 60 of the anchor. The pusher member is then withdrawn and the suture tensioned to move the anchor to the position shown in FIG. 2 in a manner similar to that described in the aforementioned U.S. Pat. Nos. 5,527,343 and 5,534,012.

Although it is believed that it may be preferred to change the orientation of the anchor 50 after it has emerged from the passage 40, the anchor could be blocked from reentering the passage in other ways if desired. Thus, the anchor could expand after emerging from the passage 40. This could be accomplished by having spring biased arms held in a retracted position by engagement of spring biased arms with the inner side surface of the tubular cylindrical member which lines the passage 40. Upon emerging from the passage, the arms would move outward under the influence of spring forces and extend radially outward beyond the edge of the exit from the passage 40. If desired, the anchor 50 could be constructed so as to expand in a manner similar to that disclosed in U.S. Pat. No. 5,397,331 and/or U.S. Pat. No. 4,409,974.

Rather than expanding under the influence of stored energy, such as spring force, the anchor 50 could expand by absorbing body fluids. Thus, the anchor 50 may be compressed when it moves through the passage 40 and will expand and absorb body fluids after emerging from the passage 40. It is contemplated that the anchor 50 could be constructed so as to expand in any one of the ways disclosed in U.S. patent application Ser. No. 08/699,553 filed Aug. 19, 1996 by Peter M. Bonutti and entitled "Suture Anchor".

The cylindrical tubular member is then withdrawn from the passage 40. It should be understood that the cylindrical tubular member is used to line the passage 40 in the bone 20 during movement of the anchor 50 through the passage. The use of the tubular member to line the passage 40 may be omitted if desired. However, if the use of the tubular member to line the passage 40 is omitted, the anchor 50 and pusher member would be exposed to the cancellous bone tissue 44 during movement of the anchor through the passage.

The limbs 72 and 74 of the suture 38 are then threaded through openings 64 and 66 in the second suture anchor 52.

The limbs 72 and 74 of the suture 38 are tensioned and the second anchor 52 is pressed against the outer side surface of the bone 20. While a predetermined tension force is maintained in the limbs 72 and 74 of the suture 38, the knot 78 is tied in the suture to interconnect the two suture anchors 50 and 52 with the suture 38. The suture 38 is then trimmed to the desired length.

Once the knot 78 has been tied between the limbs 72 and 74 of the suture 38, the tension in the suture 38 presses the side surfaces 28 and 30 of the fracture 26 together. This pressure between the side surfaces 28 and 30 of the fracture 26 is maintained by the suture 38 and suture anchors 50 and 52 until the fracture heals. It is believed that it may be preferred to form the suture 38 and suture anchors 50 and 52 of a biodegradable material which, after the fracture 26 has healed, will dissolve in the patient's body.

The cylindrical tubular member which is inserted into the passage 40 through the bone 20 performs the dual functions of lining the inside of the passage 40 and maintaining the two sections 22 and 24 of the bone in alignment. The cylindrical tubular member could have a slot formed in a side wall of the tubular member to facilitate insertion of the tubular member into the passage 40. It is contemplated that the cylindrical tubular member could be left in the passage 40 after the bone suture assembly 32 has been installed. If the slotted or unslotted cylindrical tubular member is to be left in the passage 40, the cylindrical tubular member may be formed of a biodegradable or bioerodible copolymer. When the cylindrical tubular member remains in the passage 40, the suture 38 extends through the tubular member.

Although only a knot 78 has been shown in FIG. 2 adjacent to the second anchor 52, a suture retainer could be provided to further hold the limbs 72 and 74 of the suture 38. If a suture retainer is to be used in association with the knot 78, the suture retainer will be moved along the limbs of the suture 38 toward the knot before the limbs 72 and 74 of the suture are trimmed to the short length shown in FIG. 2. The suture retainer would then be plastically deformed to grip the limbs 72 and 74 of the suture 38. Thereafter, the suture limbs 72 and 74 would be trimmed to a desired length.

Bone Suture Assembly—Second Embodiment

In the embodiment of the invention illustrated in FIG. 2, a pair of suture anchors 50 and 52 are connected with the suture 38 to maintain tension in the suture and pressure against opposite side surfaces 28 and 30 of the fracture 26. In the embodiment of the invention illustrated in FIG. 3, a suture retainer is used in place of one of the suture anchors. Since the embodiment of the invention illustrated in FIG. 3 is generally similar to the embodiment of the invention illustrated in FIG. 2, similar numerals will be utilized to designate similar components, the suffix letter "a" being associated with the embodiment of the invention illustrated in FIG. 3 to avoid confusion.

A bone 20a has sections 22a and 24a which are separated by a fracture 26a. The fracture 26a has side surfaces 28a and 30a which are pressed together by a bone suture assembly 32a. A suture 38a extends through a cylindrical passage 40a which extends diametrically through the generally cylindrical bone 20a. The suture 38a has a pair of limbs or sections 72a and 74a which are connected with a suture anchor 50a. The suture anchor 50a has the same construction as the suture anchor 50 of FIG. 2.

In accordance with a feature of this embodiment of the invention, a suture retainer 92 is used in place of the suture anchor 52 of FIG. 2. The suture retainer 92 has a spherical configuration. A cylindrical passage 94 extends through the center of the spherical suture retainer 92. The sections 72a and 74a of the suture 38a extend around the spherical outer side surface of the suture retainer 92. Thus, a loop is formed in each of the sections 72a and 74a around portions of the suture retainer 92.

If desired, the suture retainer 92 could have a different configuration. For example, the suture retainer 92 could have an oval or elliptical configuration. Although the passage 94 has a linear central axis, the passage could have a nonlinear central axis. If desired, a plurality of passages having the same or different configurations could be provided in the suture retainer 92.

After the suture 38a has been inserted through the suture retainer 92, in the manner illustrated schematically in FIG. 3, the suture retainer 92 is moved along the sections 72a and 74a of the suture 38a toward the bone 20a. The suture retainer 92 is formed as one piece of a polymeric material having a relatively low coefficient friction. Therefore, the two sections 72a and 74a of the suture 30a can readily slide along the surfaces of the suture retainer 52a while the suture retainer moves toward the bone 20a.

A predetermined tension is maintained in the sections 72a and 74a of the suture 38a while the suture retainer 92 is pressed against the bone 20a. This results in the suture 38a being pulled tightly against the suture anchor 50a. The tension in the suture 38a is effective to press the suture anchor 50a and retainer 92 against opposite sides of the bone 20a with a predetermined force.

Once the suture retainer 92 has been moved along the suture 38a and is being pressed against the bone 20a with a predetermined force, the suture retainer is plastically deformed to grip the sections 72a and 74a of the suture 38a. An apparatus 98 for pressing the suture retainer 92 against the bone 20a includes a tubular cylindrical plunger 102 (FIG. 3) having a cylindrical central passage through which the sections 72a and 74a of the suture 38a extend. The plunger 102 is enclosed by a tubular cylindrical housing 106. The plunger 102 is pressed downward, relative to the housing 106 with a predetermined force, indicated by arrows 108 and 110 in FIG. 3. An annular transducer or load cell 114 provides an output indicative of the magnitude of the force 108 and 110 with which the suture retainer 92 is pressed against the bone 20a by the plunger 102.

While the sections 72a and 74a of the suture 38a are being tensioned with a predetermined force and while the plunger 102 is being pressed against the suture retainer 92 with a predetermined force, the suture retainer 92 is plastically deformed. To plastically deform the suture retainer 92, a plurality of force applying or clamp members 120 and 122 are pressed against the suture retainer 92 with a predetermined minimum force, indicated schematically by arrows 126 in FIG. 3. The force application members 120 and 122 may have an arcuate configuration to conform to the spherical configuration of the suture retainer 92 or may have a flat configuration. The force applied against the suture retainer 92 by the force applying members 120 and 122 is sufficient to cause plastic deformation of the material of the suture retainer.

The force 126 is applied against the suture retainer 92 while the suture retainer is at a temperature which is below the transition temperature of the biodegradable polymer which forms the suture retainer 92. Thus, the suture retainer 92 is at approximately the same temperature as the bone 20a when the force 126 is applied against the suture retainer. The force 126 causes the material of the suture retainer 92 to flow and grip the sections 72a and 74a of the suture 38a.

Upon disengagement of the force application members 120 and 122 from the suture retainer 92, the application of downward (as viewed in FIG. 3) force against the suture retainer 92 is interrupted. The upward tensioning of the sections 72a and 74a of the suture 38a is also interrupted. At this time, the plastically deformed suture retainer 92 securely grips the two sections 72a and 74a of the suture 38a to maintain the tension in the suture 38a. If desired, a knot may be formed between the sections 72a and 74a of the suture as additional protection against the suture working loose over an extended period of time.

The suture retainer 92 may be formed of many different materials. However, it is believed that it will be preferred to form the suture retainer 92 of a biodegradable polymer. One biodegradable polymer which may be utilized is polycaperlactone. Alternatively, the suture retainer 92 could be formed of polyethylene oxide terephthalate or polybutylene terephthalate. It is also contemplated that other biodegradable or bioerodible copolymers could be utilized.

Although it is preferred to form the suture retainer 92 of a biodegradable material, the suture retainer could be formed of a material which is not biodegradable. For example, the suture retainer 92 could be formed of an acetyl resin, such as "DELRIN" (trademark). Alternatively, the suture retainer 92 could be formed of para-dimethylamino-benzenediazo sodium sulfonate, such as "DEXON" (trademark). The construction of the suture retainer 92 and the manner in which is cooperates with the suture 38a is the same as is disclosed in U.S. patent application Ser. No. 08/905,084 filed Aug. 1, 1997 by Peter M. Bonutti et al. and entitled "Method and Apparatus for Securing a Suture".

The suture retainer 92 is plastically deformed to grip the limbs 72a and 74a of the suture 38a. However, the suture retainer 92 could be constructed so as to be mechanically actuated to grip the suture 38a. If desired, a combination of a mechanical gripping action and plastic deformation could be utilized by a retainer to grip the suture 38a.

Retaining Body Tissue against Bone

In the embodiment of the invention illustrated in FIG. 2, a bone suture assembly 32 is utilized to press surfaces 28 and 30 of a fracture 26 together. In the embodiment of the invention illustrated in FIG. 4, the suture anchor assembly is utilized to hold body tissue against movement relative to a bone. Since the embodiment of the invention illustrated in FIG. 4 is generally similar to the embodiments of the invention illustrated in FIGS. 2 and 3, similar numerals will be utilized in association with similar components, the suffix letter "b" being associated with the numerals of FIG. 4 to avoid confusion.

A cylindrical passage 40b extends diametrically through a generally cylindrical bone 20b. A bone suture assembly 32b is utilized to retain body tissue 132 against movement relative to the bone 20b. The body tissue 132 may be a muscle, ligament, cartilage or other tissue which is to be held against movement relative to the bone 20b.

The bone suture assembly 32b includes a first suture anchor 50b and a second suture anchor 52b. A suture 38b extends through the passage 40b and interconnects the suture anchors 50b and 52b. Tension in the suture 38b presses the body tissue 132 against a side surface area on the bone 20b. The suture 38b has sections or limbs 72b and 74b which extends through openings in the suture anchors 50b and 52b in the manner previously explained. A knot 78b interconnects the sections 72b and 74b of the suture 38b to press the suture anchor 52b firmly against the body tissue 132. Although the illustrated suture has a pair of sections 72b and 74b, the suture could have a single section if desired.

The suture anchor assembly 32b is installed in association with the bone 20b and body tissue 132 in the same manner as previously explained in conjunction with the embodiment of the invention illustrated in FIG. 2. Thus, the passage 40 (FIG. 4) is formed in the bone 20*b* by drilling or other methods. The body tissue 132 may be offset to one side of the location where the passage 40*b* is formed during formation of the passage. This enables the passage 40*b* to be formed in the bone 20*b* without damaging the body tissue 132.

The suture anchor 50*b* is moved through the passage 40*b* with a longitudinal central axis of the suture anchor aligned with the longitudinal central axis of the passage 40*b*. When the suture anchor 50*b* emerges from the passage 40*b*, the anchor is pivoted to the orientation shown in FIG. 4. Alternatively, the anchor 50*b* may be mechanically expanded after emerging from the passage 40*b*. A cylindrical tubular member may be used to line the passage 40*a* during movement of the anchor 50*b* through the passage in the manner previously described in connection with the embodiment of FIG. 2.

After the anchor 50*b* has been moved to the position shown in FIG. 4, the body tissue 132 is positioned between the limbs 72*b* and 74*b* of the suture 38*b*. The limbs 72*b* and 74*b* of the suture 38*b* are then inserted-through the openings in the suture anchor 52*b*. While a predetermined tension is maintained in the suture 38*b*, the knot 78*b* is tied between the limbs 72*b* and 74*b* of the suture. This results in the body tissue 132 being pressed against the bone 20*b* with a predetermined force. A button or other force distributing member may be provided between the suture anchor 52*b* and body tissue 132 if desired.

In the embodiment of the invention illustrated in FIG. 4, two suture anchors 50*b* and 52*b* are utilized to press the body tissue 132 against the bone 20*b*. However, a suture retainer could be substituted for one or more of the suture anchors 50*b* or 52*b*. For example, a suture retainer having the same construction and installed in the same manner as the suture retainer 92 of FIG. 3 could be substituted for the anchor 52*b* of FIG. 4. It should be understood that the suture retainer substituted for the anchor 52*b* of FIG. 4 could have any desired construction. Thus, a suture retainer having the construction of any one of the suture retainers disclosed in the aforementioned U.S. patent application Ser. No. 08/905, 084, filed Aug. 1, 1997 by Peter M. Bonutti et al. and entitled "Method and Apparatus for Securing a Suture" could be utilized in place of the anchor 52*b* and/or the anchor 50*b*.

When a suture retainer is used in place of the anchor 52*b*, the suture retainer applies force against the body tissue 132 to press the body tissue against the bone 20*b*. If desired, a force distribution member could be provided between the suture retainer and the body tissue 132.

Although the passage 40*b* has been illustrated in FIG. 4 as having a linear configuration, the passage could have a nonlinear configuration if desired.

In the embodiment of the invention illustrated in FIG. 4, body tissue 132 is disposed adjacent to only one side of the bone 20*b*. However, if desired, body tissue could be disposed adjacent to opposite sides of the bone 20*b*. The body tissue could be connected with the anchor 50*b* in many different ways. For example, a separate length of suture could be connected with the body tissue and anchor 50*b* or with the suture 38*b* adjacent to the anchor 50*b*.

An alternative manner of connecting body tissue with the side of the bone adjacent to the anchor 50*b* would be to insert the body tissue between the limbs 72*b* and 74*b* of the suture 36*b* in the same manner as shown with the anchor 52*b*. If this is to be done, an end portion of the body tissue may be manually inserted between the limbs 72*b* and 74*b* of the suture 38*b*. If a central portion of the body tissue is to be disposed between the anchor 50*b* and the bone 20*b*, the connector section 76*b* of the suture could be cut. One of the limbs 72*b* or 74*b* of the suture would then be separated from the anchor 50*b*. The body tissue would be inserted between the limbs of the suture 38. The separated end of the suture would then be inserted through the anchor 50*b* and connected with the other limb of the suture 38*b*.

In the embodiment of the invention illustrated in FIG. 4, the body tissue 132 is pressed against a bone 20*b* which has not been fractured. However, it is contemplated that the bone suture assembly 32 could be utilized to perform the dual functions of pressing body tissue against a bone and of pressing opposite side surfaces of a fracture together. This would result in the body tissue being pressed against the bone 20*b* in the manner illustrated in FIG. 4 and in opposite side surfaces of a fracture being pressed together in the manner illustrated in FIG. 2 for the opposite side surfaces 28 and 30 of the fracture 26.

Nonlinear Suture Passage

In the embodiment of the invention illustrated in FIG. 2, the passage 40 through which the suture 38 extends has a linear configuration. In the embodiment of the invention illustrated in FIG. 5, the passage through which the suture extends has a nonlinear configuration. Since the embodiment of the invention illustrated in FIG. 5 is generally similar to the embodiment of the invention illustrated in FIGS. 2–4, similar numerals will be utilized to identify similar components, the suffix letter "c" being associated with the components of the embodiment of the invention illustrated in FIG. 5 to avoid confusion.

A bone 20*c* as a fracture 26*c* which divides the bone into two sections 22*c* and 24*c*. Opposite side surfaces 28*c* and 30*c* of the fracture 26*c* are pressed together by a bone suture assembly 32*c*. The bone suture assembly 32*c* includes a suture 38*c* which extends between first and second suture anchors 50*c* and 52*c*.

In accordance with a feature of this embodiment of the invention, the suture 38*c* is disposed in a passage 40*c* having a nonlinear configuration. Thus, the passage 40*c* includes a first section 140 which is skewed relative to a second section 142 of the passage 40*c*. A bend 144 is formed in the passage 40*c* at an intersection 146 of the first and second sections 140 and 142 of the passage 40*c*. The flexible suture 38*c* extends around the bend 144 along a nonlinear path between the suture anchors 50*c* and 52*c*. At the bend 144, the suture 38*c* applies force against the section 24*c* of the bone 20*c* urging the section 24*c* toward the left (as viewed in FIG. 5). This force presses the sections 22*c* and 24*c* of the bone 20*c* firmly together at the fracture 26*c*.

The suture anchors 50*c* and 52*c* have the same cylindrical construction as the suture anchors 50 and 52 in the embodiment of the invention illustrated in FIG. 2. A knot 78*c* (FIG. 5) is provided between limbs of the suture 38*c* to maintain a desired tension in the suture 38*c*. This tension pulls the suture anchors 50*c* and 52*c* toward each other. In addition, this tension presses the section 24*c* of the bone 20*c* firmly against the section 22*c* of the bone at the fracture 26*c*.

The first section 140 of the passage 40*c* is formed at an angle to and extends through a longitudinal central axis of the generally cylindrical bone 20*c*. The second section 142 of the passage 40*c* is formed in a direction perpendicular, i.e., along a radius, of the generally cylindrical bone 20*c*. The two sections 140 and 142 of the passage 40*c* terminate in the spongy cancellous bone tissue 44*c*.

When the suture assembly 32*c* is to be used to treat the fracture 26*c* in the bone 20*c*, the two sections 22*c* and 24*c* of the bone are pressed together at the fracture 26c to align the side surfaces 28c and 30c of the fracture. A drill or other hole forming apparatus is then used to form the first section 140 of the passage 40c. The drill or other hole forming apparatus is then used to form the second section 142 of the passage 40c. When the second section 142 of the passage 40c intersects the first section 140 of the passage 40c, formation of the section 142 of the passage 40c is interrupted.

Once the nonlinear passage 40c has been formed in the two sections 22c and 24c of the bone 20c, a tubular cylindrical liner (not shown) is inserted into the passage 40c. The tubular cylindrical liner may be formed by two separate tubular members which are inserted at opposite ends of the passage 40c. Alternatively, the tubular cylindrical liner may be formed by a single flexible tubular member which is inserted into the section 140 of the passage 40c and then moved around the bend 144 into the section 142 of the passage 40c. It should be understood that the tubular cylindrical liner for the passage 40c could be omitted if desired.

The cylindrical anchor 50c, with the suture 38c connected thereto, is then positioned in axial alignment with the section 142 of the passage 40c. The leading end 58c of the anchor 50c is then moved into the lined section 142 of the passage 40c. A flexible pusher member applies force against the trailing end 60c of the anchor 50c and pushes the anchor around the bend 144 and through the section 140 of the passage 40c.

Alternatively, a flexible wire or other member could be inserted into the section 140 of the passage 40c. The wire would move around the bend 144 and extend outward from the section 142 of the passage. The wire would then be connected with the anchor 50c and suture 38c. The leading end 58c of the anchor 50c would then be inserted into the section 142 of the passage 40c. Tension on the wire would pull the anchor 50c around the bend 144 and out of the section 140 of the passage 40c.

Once the anchor 50c has been moved out of the passage 40c, the tubular liner for the passage may be withdrawn. If a one-piece tubular liner is used, it may be withdrawn from the open end of the section 142 of the passage 40c. If a two-piece liner is used, one of the pieces may be withdrawn from the open end of the passage section 140 and slit to clear the suture 38c. Alternatively, the slit could be formed in the piece of the liner before it is inserted into the passage section 140. The other piece of the liner would be withdrawn from the open end of the passage section 142. Alternatively, the tubular liner for the passage 40c may be left in place. Of course, the use of a tubular liner for the passage 40c may be omitted.

The suture 38c is then threaded through openings in the suture anchor 52c. The suture 38c is then tensioned and the second anchor 52c is pressed against the outer side surface of the bone 20c. While a predetermined tension force is maintained in the suture 38c, the knot 78c is tied.

In the illustrated embodiment of the invention, the two sections 140 and 142 of the passage 40c have a straight cylindrical configuration. However, it is contemplated that the sections 140 and 142 of the passage 40c could have a different configuration if desired. For example, the section 140 and/or 142 of the passage 40c could have a nonlinear central axis and could have a noncircular cross-sectional configuration of desired.

Body tissue, corresponding to the body tissue 132 of FIG. 4 could be disposed between the anchor 50c and/or 52c and the bone 20c. Although the suture 38c has been illustrated as having a pair of limbs or sections which extend between the anchors 50c and 52c, the suture 38c could have a single limb or section if desired. The anchor 50c could mechanically expand, by absorbing body liquid or under the influence of expansion springs, after the anchor has emerged from the passage 40c to prevent the anchor from being pulled back through the passage.

Nonlinear Passage—Second Embodiment

In the embodiment of the invention illustrated in FIG. 5, the bone suture assembly 32c associated with the nonlinear passage 40c includes a pair of suture anchors 50c and 52c. In the embodiment of the invention illustrated in FIG. 6, a suture retainer in substituted for one of the suture anchors in much the same manner as previously described in conjunction with the embodiment of the invention illustrated in FIG. 3. Since the embodiment of the invention illustrated in FIG. 6 is generally similar to the embodiment of the invention illustrated in FIGS. 2–5, similar numerals will be utilized to designate similar components, the suffix letter "d" being associated with the numerals of FIG. 6 in order to avoid confusion.

A bone 20d has a fracture 26d which divides the bone into two sections 22d and 24d. The fracture 26d has side surfaces 28d and 30d which are pressed together by a bone suture assembly 32d. The bone suture assembly 32d includes a suture 38d which extends through a nonlinear passage 40d having the same construction as the nonlinear passage 40c of FIG. 5.

In accordance with a feature of this embodiment of the invention, the bone suture assembly 32d includes a suture anchor 50d having the same construction as the suture anchor 50 of FIG. 2, and a suture retainer 92d having the same construction as the suture retainer 92 of FIG. 3. The suture anchor 50d and suture retainer 92d maintain a predetermined tension in the suture 38d. This results in the suture anchor 50d being firmly pressed against the section 24d of the bone 20d. The suture retainer 92d is firmly pressed against the section 22d of the bone 20d by the tension in the suture 38d.

Since the passage 40d has a nonlinear configuration, the suture 38d is effective to apply a force component to the section 24d of the bone 20d urging the section 24d of the bone toward the left (as viewed in FIG. 6). This results in the surface 30d of the fracture 26d being pressed firmly against the surface 28d of the fracture.

The suture retainer 92d is plastically deformed to grip the suture 38d in the same manner as previously described herein in conjunction with the suture retainer 92 of FIG. 3. However, the suture retainer 92d could be constructed so as to form a mechanical connection with the suture 38d. If desired, a suture retainer could be substituted for the anchor 50d.

Although both the suture retainer 92d and anchor 50d have been illustrated in FIG. 6 as being disposed in engagement with the bone 20d, a force distributing member could be provided between the anchor and/or suture retainer and the bone. It is contemplated that body tissue, similar to the body tissue 132 of FIG. 4, could be disposed between the anchor 50d and/or the suture retainer 92d and the bone 20d.

Tissue Tensioning With Bone Fragment Retaining

In the embodiment of the invention illustrated in FIG. 2, the fracture in a portion of a bone is treated. In the embodiment of the invention illustrated in FIGS. 7 and 8, a fracture results in a fragment of a bone being separated from a main portion of the bone. The bone fragment is connected with the main portion of the bone by muscle, tendon, ligament, cartilage or other fibrous body tissue. In the embodiment of the invention illustrated in FIGS. 7 and 8, the fibrous body tissue is tensioned as the bone fragment is positioned relative to the main portion of the bone. Since the embodiment of the invention illustrated in FIGS. 7 and 8 is generally similar to the embodiment of the invention illustrated in FIGS. 2–6, similar numerals will be utilized to designate similar components, the suffix "e" being associated with the numerals of FIGS. 7 and 8 in order to avoid confusion.

A bone fragment 154 is separate from a main bone 20e (FIG. 7). The fragment 154 is connected with the main bone 20e by fibrous body tissue 158, i.e., muscle, tendon, ligament, cartilage, etc. The fibrous body tissue 158 extends between the bone fragment 154 and a portion 160 of the main bone 20e. The bone fragment 154 has a side surface 28e with a configuration which matches the configuration of a side surface 30e of a fracture 26e which occurred in the main bone 20e.

In order to promote healing of the main bone 20e, a bone suture assembly 32e (FIG. 8) is utilized to pull the bone fragment 154 toward the main bone 20e. As this occurs, the fibrous body tissue 158 is tensioned and the side surface 28e on the bone fragment 154 is pressed against the side surface 30e on the main bone 20e. The bone fragment 154 is pressed firmly against the main bone 20e by the bone suture assembly 32e. Thus, the gap illustrated schematically in FIG. 8, between the side surfaces 28e and 30e of the fracture 26e, is eliminated and the side surfaces of the fracture are pressed firmly together by the bone suture assembly 32e. If desired, the bone fragment 154 may be manually pressed against the main bone 20e before the bone suture assembly is pulled tight.

The bone suture assembly 32e includes a suture 38e having limbs or sections 72e and 74e. The suture 38e extends through openings in a first suture anchor 50e. The suture then extends into a passage 40e formed in the bone fragment 154 and the main bone 20e.

The passage 40e includes a first section 140e which extends through the bone fragment 154. In addition, the passage 40e includes a second section 142e which extend through the main bone 20e. The limbs or section 72e and 74e of the suture 38e extends through a second anchor 52e.

During installation of the bone suture assembly 32e, the limbs 72e and 74e of the suture 38e are gripped by a force or tension measurement device 98e. The tension measurement device 98e includes a load cell which measures the amount of tension applied to the limbs 72e and 74e of the suture 38e.

As tension is applied to the limbs 72e and 74e of the suture 38e, the bone fragment 154 is pulled toward the right (as viewed in FIG. 8) to move the side surface 28e on the bone fragment into alignment with the side surface 30e on the main bone 20e. As this occurs, the fibrous body tissue 158 is stretched or tensioned. While a predetermined force is transmitted through the limbs 72e and 74e to the suture anchor 50e and the bone fragment 154 to firmly press the bone fragment against the main bone 20e, a knot 78e is tied to interconnect the limbs 72e and 74e. While the predetermined tension is maintained and the knot 78e tied, the second anchor 52e is firmly pressed against the side surface of the main bone 20e.

Although the passage 40e could have a linear configuration if desired, in the embodiment of the invention illustrated in FIG. 8, the passage 40e has a nonlinear configuration. Thus, the first section 140e of the passage 40e has a central axis which is skewed relative to a central axis of the second section 142e of the passage 40e. This enables the flexible suture 38e to apply force to the bone fragment 154 having components urging the bone fragment rightward (as viewed in FIG. 8) against the surface 30e on the main bone 20e and downward (as viewed in FIG. 8) to maintain the tension in the fibrous body tissue 158.

When the passage 40e is to be formed in the bone fragment 154 and main bone section 20e, a hole is drilled through the bone fragment 154 to form the first section 140e of the passage. The second portion 142e of the passage 40e is drilled in the main bone 20e. It should be understood that the passage 40e could be formed in many different ways other than drilling. For example, a cutting tool or laser could be used to form the passage 40e.

The second section 142e of the passage 40e has a longitudinal central axis which is skewed at an acute angle relative to the longitudinal central axis of the first section 140e of the passage in the bone fragment 154. Thus, the first portion 140e of the passage 40e in the bone fragment 154 has a central axis which is close to being perpendicular to a longitudinal central axis of the main bone 20e. The second portion 142e of the passage 40e has a longitudinal central axis which is angularly offset to a substantial arc relative to the longitudinal central axis of the main bone 20e.

The anchor 50e is moved through the first section 140e of the passage 40e and positioned in engagement with an outer side surface of the bone fragment. The free ends of the limbs 72e and 74e of the suture 38e are then moved rightward (as viewed in FIG. 8) through the second portion 142e of the passage 40e. The free ends of the suture 38e are then threaded through openings in the second anchor 52e.

After the suture 38e has been inserted through openings in the second anchor 52e, the force or tension measuring device 98e is utilized to pull the free ends of the suture 38e toward the right (as viewed in FIG. 8). This tension pulls the bone fragment 154 into engagement with the main bone 20e. The knot 78e is tied in the free ends of the suture 38e while the tension is maintained in the suture.

If desired, the bone suture assembly 32e could be positioned relative to the bone 20e and the bone fragment 154 by moving the anchor 50e first through the second section 142e of the passage disposed in the main bone 20e and then through the first section 140e of the passage disposed in the fragment 154. The free ends of the suture would then be inserted through the second anchor 52e. The suture 38e would be tensioned to pull the bone fragment 154 into place with the side surface 28e in aligned engagement with the surface 30e on the main bone 20e. The knot 78e would then be tied while maintaining the desired tension in the suture 38e.

It should be understood that the anchor 52e and knot 78e could be positioned adjacent to the bone fragment 154 and the anchor 50e positioned adjacent to the bone 20e. Although only a single bone suture assembly 32e has been illustrated in FIG. 8, multiple bone suture assemblies could be used to position the bone fragment 154 relative to the bone 20e.

In the embodiment of the invention illustrated in FIGS. 7 and 8, the bone suture assembly 32e includes a pair of anchors 50e and 52e. If desired, a suture retainer could be substituted for either or both of the anchors 50e and 52e. Thus, a suture retainer having a construction similar to the construction of the suture retainer 92 of FIG. 3 could be used in place of the second anchor 52e. It should be understood that the suture retainer 92 could have the same construction as any one of the suture retainers disclosed in the aforementioned U.S. patent application Ser. No. 08/905,084 filed Aug. 1, 1997 by Peter M. Bonutti et al. and entitled "Method and Apparatus for Securing a Suture".

In the embodiment of the invention illustrated in FIG. 8, the anchors 50e and 52e are placed in engagement with the bone of fragment 154 and main bone 20e. However, it is contemplated that the anchor 50e and/or 52e could be positioned in engagement with body tissue other than bone. For example, the anchor 50e could be positioned in engagement with a portion of the fibrous body tissue 158 to position the fibrous body tissue 158 relative to the bone fragment 154 and to more securely interconnect the fibrous body tissue and the bone fragment. If desired, body tissue could be positioned between the anchor 52e and the main bone 20e.

In FIG. 8, there is a single bone fragment 154. However, fractures may occur in such a manner as to have a plurality of bone fragments. A plurality of bone suture assemblies 32e could be utilized to interconnect the plurality of bone fragments and the main bone.

When a fracture occurs in such a manner as to form a plurality of bone fragments, it may be desired to use bone suture assemblies 32e in association with only the larger bone fragments. If desired, a bridge or cover member could extend across the bone fragments to position the bone fragments relative to each other. One or more bone suture assemblies 32e would extend through one or more of the larger bone fragments and through the bridge or cover member. Force applied against the bridge or cover member by an anchor or anchors in a bone suture assembly or assemblies 32e would urge the bridge or cover member toward the main bone 20e to position the smaller bone fragments relative to the larger bone fragments and main bone 20e and to press the bone fragments against each other and against the main bone.

One or more of the anchors 50e and 52e could be formed of body tissue or of material which absorbs body fluid and expands. Alternatively, one or more of the anchors 50e or 52e could be mechanically expanded to block movement into the passage 50e.

Bone Fragment Retention

In the embodiment of the invention illustrated in FIG. 2, the bone suture assembly 32 extends between diametrically opposite outer side surface areas on the bone 20. This results in the first suture anchor 50 being disposed against an outer side surface of the hard outer layer 42 of the bone 20 (FIG. 1) and the suture anchor 52 being disposed against the outer side surface of the hard outer layer 42 on the opposite side of the bone. In the embodiment of the invention illustrated in FIG. 9, one of the anchors is disposed within the bone and the other anchor is disposed outside of the bone. Since the embodiment of the invention illustrated in FIG. 9 is generally similar to the embodiment of the invention illustrated in FIGS. 2–8, similar numerals will be utilized to identify similar components, the suffix letter "f" being associated with the numerals of FIG. 9 in order to avoid confusion.

A bone 20f has a hard outer layer 42f which encloses spongy cancellous bone tissue 44f. A fragment 164 has broken away from the hard outer layer 42f. A bone suture assembly 32f is used to position and hold the fragment 164 in engagement with the bone 20f. The bone suture assembly 32f includes a first suture anchor 50f which is disposed in engagement with an inner side surface 166 of the outer layer 42f of bone. A second anchor 50f is disposed in engagement with an outer side surface 168 of the fragment 164. A suture 38f extends between the first and second anchors 50 and 52f. The suture 38f extends through a passage 40f which extends across a fracture 26f.

When the bone suture assembly 32f is used to position the fragment 164 against the outer layer 42f of the bone 20f, the fragment 164 is aligned with the outer layer 42f of the bone 20f. At this time, a side surface 172 on the fragment 164 is disposed in aligned engagement with a side surface 174 on the bone 20f. The two side surfaces 172 and 174 were formed by breaking away of the fragment 164 from the outer layer 42f of the bone.

Once the fragment 164 has been aligned with the bone 20f, the linear passage 40f is formed by drilling or other methods through the fragment 164 and the outer layer 42f of bone. A cylindrical tubular member (not shown) having a thin cylindrical side wall is then inserted through the passage 40f. The first anchor 50f is moved to an orientation in which a longitudinal central axis of the first anchor is aligned with a longitudinal central axis of the cylindrical tubular member.

The first anchor 50f is then moved through the cylindrical tubular member, across the fracture 26f and into the spongy cancellous bone tissue 44. A pusher member applies force against a trailing end of a first anchor 50f to push the anchor through the tubular member. When the leading end of the first anchor 50f emerges from the passage 40f, the longitudinal central axis of the first anchor is aligned with the longitudinal central axis of the passage 40f.

The first anchor 50f is then pivoted through 90° to change its orientation to the orientation shown in FIG. 9. The tubular member is then withdrawn from the passage 40f. The free ends of the suture 38f are then inserted through openings in the anchor 52f. The suture is tensioned to press the anchor 50f against the inner side surface 166 on the outer layer 42f of the bone 20f. The second anchor 52f is pressed against the outer side surface 168 or the fragment 164 with a predetermined force by the tension in the suture 38f. A knot 78f is then tied in the free ends of the suture 38f to maintain the desired tension in the suture.

Although it is believed that it may be desired to remove the tubular member from the passage 40f, the tubular member could be left in the passage if desired. If the tubular member is to be left in the passage 40f, the tubular member may be formed of a biodegradable or bioerodible copolymer. Of course, the use of the tubular member could be eliminated if desired.

It should be understood that a suture retainer, having a construction similar to the construction of the suture retainer 92 of FIG. 3, could be used in place of the second anchor 52f if desired. Although the suture anchor 52f has been shown in FIG. 9 as being disposed in direct abutting engagement with the outer side surface 168 of the bone fragment 164, a layer of body tissue could be provided between the suture anchor 52f and the outer side surface 168 of the bone fragment 164 to hold the body tissue against movement relative to the bone 20f. If desired, a plurality of bone suture assemblies 32f could be utilized to hold the bone fragment 164.

Use of Plates with Bone Suture Assembly

In the embodiment of the invention illustrated in FIG. 2, the suture anchors 50 and 52 are disposed in abutting engagement with an outer side surface of a bone. In the embodiment of the invention illustrated in FIG. 10, a pair of bone plates and rigid fasteners are used in association with a bone suture assembly. Since the embodiment of the invention illustrated in FIG. 10 is generally similar to the embodiment of the invention illustrated in FIGS. 2–9, similar numerals will be utilized to designated similar components, the suffix "g" being associated with the numerals of FIG. 10 to avoid confusion.

A bone 20g has sections 22g and 24g which are separated by a fracture 26g. In accordance with a feature of this embodiment of the invention, a pair of plate members 184 and 186 are used in association with a bone suture assembly 32g. The plate members 184 and 186 may be formed of any desired biocompatible material. Thus, the plate members may be formed of metal or a polymeric material. If the plate members 184 and 186 are formed of polymeric material, biodegradable or bioerodible copolymers could be utilized.

In the illustrated embodiment of the invention, the plate members 184 and 186 are rigid and are shaped to engage the bone 20g. If desired, the plate members 184 and 186 could have sufficient flexibility to enable the plate members to be plastically deformed to the configuration of the bone 20g after having been positioned in engagement with the bone.

A first suture anchor 50g is pressed against the plate member 184 by tension in a suture 38g. The suture 38g extends through a passage 40g in the bone 20g. A second anchor 52g is pressed against the plate member 186 by the tension in the suture 38g. A knot 78g is provided in the suture 38g.

A pair of screws 190 and 192 extend diametrically through the bone 20g between the plate members 184 and 186. The screws 190 and 192 are engaged by nuts 196 and 198 which engage the plate member 184. The screws 190 and 192 and nuts 196 and 198 cooperate to press the plate members 184 and 186 against the bone 20g. If desired, bone suture assemblies having the same construction as the bone suture assembly 32g could be substituted for the screws 190 and 192 and nuts 196 and 198 so that the plates 184 and 186 would be held in position against the bone 20g by only the plurality of bone suture assemblies 32g.

The screws 190 and 192 and nuts 196 and 198 may be formed of any desired biocompatible material. Thus, the screws 190 and 192 and nuts 196 and 198 may be formed of metal or a polymeric material. If the screws 190 and 192 and nuts 196 and 198 are formed of polymeric material, biodegradable or bioerodible copolymers could be utilized.

In the illustrated embodiment of the invention, the screws 190 and 192 extend through the bone 20g. It is contemplated that shorter screws could be utilized if desired. These shorter screws would have relatively coarse bone engaging thread convolutions to hold the short screws and plate members 184 and 186 in place. The shorter screws would have a length which is less than diameter of the bone 20g.

In the illustrated embodiment of the invention, the bone suture assembly 32g extends through a linear passage 40g. If desired, the passage 40g could have a nonlinear configuration. If bone suture assemblies 32g are substituted for the screws 190 and 192 and nuts 196 and 198, some of the bone suture assemblies could extend through linear passages while other bone suture assemblies extend through nonlinear passages.

Installation Method

In the embodiment of the invention illustrated in FIG. 2, the passage 40 is formed in the bone 20 by any desired method. A thin walled cylindrical tubular member is then inserted into the passage and the first suture anchor 50 moved through the thin walled member. In the embodiment of the invention illustrated in FIGS. 11 and 12, a cannulated drill is used to drill a passage through a bone and to guide movement of the first anchor through the bone. Since the embodiment of the invention illustrated in FIGS. 11 and 12 is generally similar to the embodiments of the invention illustrated in FIGS. 2–10, similar numerals will be utilized to identify similar components, the suffix "h" being associated with the numerals in FIGS. 11 and 12 to avoid confusion.

A bone 20h has a fracture (not shown). When the fracture is to be treated with a bone suture assembly 32h (FIG. 12), a thin elongated cylindrical member or K-wire 204 is first inserted through the bone 20h. This may be done by rotating the thin elongated member 204 with a drill drive mechanism in the manner indicated by an arrow 206 in FIG. 11. The drill drive mechanism is provided with a passage which extends through a drive shaft for the mechanism. While the thin elongated member 204 is being rotated by the drill drive mechanism, the K-wire extends through the passage in the drill drive mechanism.

As the thin elongated member 204 is rotated by the drill drive mechanism, it is pressed against the bone 20h. As the thin elongated member 204 is rotated, in the manner indicated by the arrow 206 in FIG. 11, the thin elongated member is moved diametrically through the generally cylindrical bone 20h until the leading end of the thin elongated member 204 extends from the opposite side of the bone. Thus, the thin elongated member 204 is moved through the hard outer layer 42h (FIG. 12) at one side of the bone 20h, through the spongy or cancellous bone tissue 44h, and through the hard outer layer at the diametrically opposite side of the bone. When this has been done, the thin elongated member 204 will extend across the fracture in the bone.

The drill drive mechanism is then disengaged from the thin elongated member 204. A cannulated drill 210 is moved axially along the thin elongated member until the leading end portion 212 of the drill 210 engages the bone 20h (FIG. 11). The drill 210 is then gripped by the drill drive mechanism.

While the thin elongated member 204 remains stationary, the drill 210 is rotated about the thin elongated member in the manner indicated by an arrow 214 in FIG. 11. As the drill 210 is rotated about the stationary thin elongated member 204, the drill is moved axially into the bone 20h. As this occurs, the leading end 212 of the drill enlarges the hole or passage formed in the bone 20h by the thin elongated member 204. The drill 210 is moved along the thin elongated member 204 until the drill extends diametrically across the bone 20h. This movement of the drill 210 is guided by engagement of the thin elongated member 204 with a side wall of a cylindrical passage 218 which extends axially through the drill 210. Movement of the drill 210 through the bone 20h forms a passage 40h which extends through a fracture in the bone.

Once the drill 210 has been moved diametrically through the generally cylindrical bone 20h (FIG. 12), the thin elongated member 204 is withdrawn from the drill. This leaves an open cylindrical passage 218 extending through the drill 210 and across the bone 20h. The passage 218 has a diameter which is just slightly greater than the diameter of a cylindrical first anchor 50h of the bone suture assembly 32h. The cylindrical first anchor 50h is axially aligned with the passage 218 in the drill 210, in the manner shown in FIG. 12. At this time, the suture 38h has been inserted through openings in the first anchor 50h and suture limbs or sections 72h and 74h extend away from the first anchor 50h, in the manner indicated schematically in FIG. 12.

A cylindrical pusher member 222 is axially aligned with the first anchor 50h and the passage 218 through the drill 210. The pusher member 222 is utilized to push the first anchor 50h through the drill 210 to the far side of the bone 20h.

As the first suture anchor 50h emerges from the passage 28 in the drill 210, the anchor is pivoted through ninety degrees. This pivotal movement changes the orientation of the anchor 50h from an orientation in which the longitudinal central axis of the anchor 50h is aligned with the longitudinal central axis of the passage 218 and drill 210 to an orientation in which a longitudinal central axis of the cylindrical anchor 50h extends perpendicular to the longitudinal central axis of the passage and drill. The manner in which the anchor 50*h* is pivoted is the same as is described in the aforementioned U.S. Pat. Nos. 5,527,343 and 5,534,012.

The pusher member 222 is then withdrawn from the drill 10 and the drill is withdrawn from the passage formed through the bone 20*h*. As this occurs, the suture 38*h* is tensioned to hold the anchor 50*h* in place against the bone 20*h*. The drill 210 is then disengaged from the suture 38*h*. The free limbs 72 and 74 of the suture 38*h* are then inserted through a second anchor corresponding to the anchor 52 in FIG. 2. While a predetermined tension is maintained in the suture 38*h*, the suture is tied to hold the second suture anchor, corresponding to the suture anchor 52 in FIG. 2, against the bone 20*h* on a side of the bone opposite from the anchor 50*h*.

In the foregoing description, the drill 210 has been a rigid drill which has been used to form a linear passage to the bone 20*h*. However, it is contemplated that a flexible drill could be utilized to drill a passage through the bone. If this was done, the drill could be guided in such a manner as to form a nonlinear passage in the bone.

The foregoing description of how the passage 40*h* is formed has been in conjunction with a bone 20*h* having a fracture similar to the fracture 26 of FIG. 2. However, it is contemplated that the thin elongated member 204 and drill 210 could be used to form a passage in a bone which has not been fractured (FIG. 4). The thin elongated member 204 and 210 could be used to form a passage which extends only part way through a bone (FIG. 9).

In the description of the embodiments of the invention illustrated in FIGS. 1–12, the suture 38 (FIG. 2) has a pair of limbs or sections 72 and 74. It is contemplated that the suture 38 could have only a single limb which would be connected at one end with the first anchor 50 and at the opposite end with the second anchor 52. This single limb could either be tied off at the second anchor 52 or gripped by a suture retainer, similar to the suture retainer 92 of FIG. 3.

In the embodiments of the invention illustrated in FIGS. 1–12, the suture 38 has been formed separately from the first suture anchor 50. It is contemplated that the first suture anchor 50 could be formed as one piece with the suture 38. For example, the suture and anchor could be formed as one piece in a manner similar to that disclosed in U.S. Pat. No. 4,669,473 or in U.S. Pat. No. 4,741,330.

The anchors 50 and 52 in the embodiment of FIGS. 2–12 could have any one of many different constructions. For example, the anchors could expand by absorbing body fluid. The anchor 50, which is moved through a passage 40 in the embodiments of FIGS. 2–12, could mechanically expand upon exiting from the passage.

Positioning of Tubular Member

In the embodiment of the invention illustrated in FIG. 13, a tubular member is positioned in the passage which extends through the bone. Since the embodiment of the invention illustrated in FIG. 13 is generally similar to the embodiments of the invention illustrated in FIGS. 1–12, similar numerals will be utilized to designate similar components, the suffix letter "j" being associated with the numerals of FIG. 13 to avoid confusion.

A bone 20*j* which has been fractured is illustrated in FIG. 1. The bone 20*j* is divided into two sections 22*j* and 24*j* by a fracture 26*j*. Opposite side surfaces 28*j* and 30*j* of the fracture 26*j* are pressed together by bone securing assemblies 32*j*.

It should be understood that the bone securing assemblies 32*j* may be utilized in the treatment of any one of many different types of fractures. The fractures may or may not result in the formation of one or more bone fragments. In FIG. 13, the bone securing assembly 32*j* has been illustrated as interconnecting sections 22*j* and 24*j* of a complete bone fracture of the spiral type. However, the bone securing assemblies 32*j* could be utilized to connect a fragment of a bone to the main portion of the bone from which the fragment was broken off.

The bone securing assembly 32*j* (FIG. 13) includes a force transmitting member 38*j* which extends across the fracture 26*j*. The force transmitting member 38*j* may be any one of many different types of force transmitting members. The force transmitting member 38*j* may be formed of human or animal body tissue. However, it is presently preferred to use a suture as the force transmitting member 38*j*. Therefore, the force transmitting member 38*j* will be referred to herein as a suture.

The suture 38*j*, that is, the force transmitting member, is disposed in a straight cylindrical passage 40*j* which extends diametrically across a generally cylindrical portion of the bone 20*j*. The passage 40*j* extends through hard compact tissue of an outer layer 42*j* of the bone and through spongy or cancellous bone tissue 44*j* which is enclosed by the hard outer layer. Although the passage 40*j* has a linear configuration, the passage could have a nonlinear configuration if desired.

The suture 38*j* extends between a first suture anchor 50*j* disposed on one side of the fracture 26*j* and a second suture anchor 52*j* disposed on the opposite side of the fracture. Tension is maintained in the suture 38*j* to press the suture anchors 50*j* and 52*j* against opposite sides of the bone 20*j* with a predetermined force. This force presses the side surfaces 28*j* and 30*j* of the fracture 26*j* firmly together to promote healing of the fracture. If desired, buttons or other force distributing members could be provided between the anchors 50*j* and 52*j* and the bone 20*j*. Body tissue could be disposed between the anchors 50*j* and 52*j* and the bone 20*j*.

The suture 38*j* and/or suture anchors 50*j* and 52*j* may be formed of any desired natural or artificial material. For example, the suture 38*j* may be formed of either a polymeric material or a metal. The suture 38*j* may be biodegradable. Any known suture material may be utilized to form the suture 38*j*.

The suture anchors 50*j* and 52*j* have the same construction. However, the anchor 50*j* could have a construction which is different than the construction of the anchor 52*j*. The anchor 50*j* has a cylindrical outer side surface 56*j* which extends between smooth rounded end portions 58*j* and 60*j*. A pair of parallel cylindrical openings 64*j* and 66*j* extend diametrically through the anchor 50*j*. The anchor 50*j* is free of sharp corners or projections to avoid cutting or abrading of body tissue disposed adjacent to the anchor.

The suture anchor 50*j* is made of a biocompatible material. Suitable materials include stainless steel or titanium, cobalt chrome and other biocompatible metals. Polymeric material may also be used, suitable polymeric materials includes polyethylene, polypropylene, and biodegradable material such as PLA and PGA. It is believed that it may be preferred to form the suture anchors 50*j* and 52*j* from biodegradable or bioerodible copolymers. If desired, the anchor 50*j* could be formed of body material or hydrophilic materials.

It is contemplated that the anchor 50*j* may have any desired configuration. For example, the anchor 50*j* could have any one of the configurations disclosed in U.S. Pat. No. 5,522,846 issued Jun. 4, 1996 and entitled "Suture Anchor". Alternatively, the suture anchor 50*j* could have the configuration disclosed in U.S. Pat. No. 5,534,012 issued Jul. 9, 1996 and entitled "Method and Apparatus for Anchoring a Suture".

The cross-sectional size of the anchor 50j may be such as to enable the anchor to be moved through the passage 40j. However, the anchor 50j could have a size and configuration which would prevent movement of the anchor 50j through the passage 40j. For example, the anchors 50j and 52j could have the same construction as the retainer 92 of FIG. 3.

The length of the anchor 50j is such as to enable it to span an opening at an end of the passage 40j and transmit force from the suture 38j to a substantial area on the outer layer 42j of the bone 20j. The length of the anchor 50j may be approximately three times the diameter of the anchor. It is believed that it will be preferred to form the anchor 50j in such a manner as to eliminate any sharp corners or projections.

In the illustrated embodiment of the invention, the anchor 50j has a cylindrical configuration. This particular anchor has an axial length of about two millimeters and a diameter of about one millimeter. The openings 64j and 66j have a diameter of about one-half millimeter.

It should be understood that the foregoing dimensions have been set forth herein for purposes of clarity of description and it is contemplated that the size of the anchor 50j may vary as a function of the size of the bone being treated. Thus, relatively small anchors may be used in association with treatment of small bones in a wrist, hand, foot or ankle of a patient. Relatively large anchors may be used in association with treatment of larger bones in an arm, shoulder, leg or hip of a patient. It should be understood that the bone securing assembly 32j may be used in conjunction with many different bones other than the specific bones previously mentioned.

Only a single anchor 50j or 52j has been shown at opposite ends of the passage 40j. It is contemplated that a plurality of anchors could be provided at each end of the passage 40j. For example, a pair of separate or interconnected anchors could be provided in a manner similar to that disclosed in the aforementioned U.S. Pat. No. 5,534,012.

In the embodiment of the invention illustrated in FIG. 13, the suture 38j has a pair of limbs or sections 72j and 74j which extend through the openings 64j and 66j in the suture anchors 50j and 52j. A connector section 76j interconnects the two limbs 72j and 74j of the suture 38j and engages a portion of the anchor 50j. A knot 78j is formed in the opposite ends of the limbs 72j and 74j to interconnect the two limbs of the suture 38j.

When the knot 78j is formed, a predetermined tension is present in the limbs 72j and 74j of the suture 38j. This results in the suture anchors 50j and 52j being pressed firmly against the bone 20j with a predetermined force. This predetermined force is maintained during and after tying of the knot 78j.

When the bone securing assembly 32j is to be used to treat the fracture 26j in the bone 20j, the two sections 22j and 24j of the bone are pressed together at the fracture 26j to align the side surfaces 28j and 30j of the fracture. A drill is then used to form the passage 40j which extends diametrically through the generally cylindrical bone 20j. Of course, the passage 40j could be formed by the use of a tool other than a drill. If desired, the passage 40j could have a noncircular cross-sectional configuration.

Once the passage 40j has been formed in the two sections 22j and 24j of the bone 20j, a tubular cylindrical member 240 is inserted into the passage 40j and extends diametrically through the bone 20j. The leading end 242 of the tubular cylindrical member 240 is aligned with a circular outlet 84j from the passage 40j. The opposite or trailing end 244 of the tubular member is aligned with a circular inlet 86j to the passage 40j. The tubular member 240 has a thin cylindrical wall which engages the sections 22j and 24j of the bone 20j. A cylindrical inner side surface of the tubular member 240 defines a cylindrical passage having a diameter which is only slightly less than the diameter of the passage 40j.

The leading end 242 of the tubular member 240 is disposed in the compact outer layer 42j of the bone 20j. Similarly, the trailing end 244 of the tubular member 240 is disposed in the compact outer layer 42j of the bone 20j. The tubular member 240 extends across the fracture 26j and stabilizes the two sections 22j and 24j of the bone 20j. Since the opposite end portions of the tubular member 240 are disposed in the compact outer layer 42j of the bone 20j, the tubular member is solidly supported and holds the two sections 22j and 24j of the bone 20j in alignment at the fracture 26j.

The opposite ends 242 and 244 of the tubular member 240 are axially spaced from a generally cylindrical outer side surface 250 on the bone 20j. This enables the anchors 50j and 52j to be pressed against the outer side surface 250 of the bone 20j. Therefore, tension forces in the suture 38j are transmitted through the anchors 50j and 52j to the bone 20j.

By inserting the tubular member 240 into the passage 40j, the portions of the passage disposed on opposite sides of the fracture 26j are maintained in alignment. The tubular member 240 may be flexible to enable the tubular member to be inserted into a nonlinear passage 40j through the bone 20j. The tubular member 240 may be formed of metal or a polymeric material. If the tubular member 240 is formed of a polymeric material, it may be preferred to form the tubular member from a biodegradable or bioerodible copolymer.

In accordance with one of the features of this embodiment of the invention, the tubular member 240 is formed of bone. By forming the tubular member 240 of bone, tissue growth into the tubular member is promoted. The tubular member 240 may be packed with bone or bone graft. The tubular member 240 may contain bone osteoinductive protein (BMP). Bone growth inducing materials containing apatite compositions with collagen and/or other materials may be utilized. The tubular member 240 may be formed of either human or animal bone.

It is contemplated that it may be preferred to form the tubular member 240 of freeze dried human bone obtained from a cadaver. The freeze dried bone will absorb body fluids. As this occurs, the tubular member 240 will expand and grip the two sections 22j and 24j of the bone 20j. The body fluids will be conducted into bone growth promoting materials contained in the tubular member 240. If desired, antibiotics and/or other medicants may be provided in the bone or bone graft with which the tubular member 240 is packed. Of course, the tubular member 240 may be formed of other materials, such as biodegradable materials, if desired.

The suture 38j is formed into a loop which extends through the openings 64j and 66j in the anchor 50j. At this time, the suture 38j has a length which is substantially greater than the length illustrated in FIG. 2. The cylindrical anchor 50j, with the suture 38j connected thereto, is then positioned in axial alignment with the tubular member 240 which extends through the passage 40j. Thus, the anchor 50j is moved to an orientation in which a longitudinal central axis of the anchor is coincident with the longitudinal central axis of the cylindrical passage 246 in the tubular member 240 which extends through the passage 40j in the bone 20j.

The leading end 58*j* of the anchor 50*j* is then moved into the cylindrical tubular member 240 which forms a liner for the passage 40*j*. A pusher member pushes the anchor 50*j* from an upper (as viewed in FIG. 13) end 244 of the tubular member 240 along the passage 246 in the tubular member 240 and the passage 40*j* in the bone 20 and through the outlet 84*j* from the passage. As the anchor 50*j* moves through the passages 40*j* and 246, the suture 38*j* is pulled through the passages by the anchor.

The orientation of the anchor 50*j* is then changed from an orientation in which the longitudinal central axis of the anchor 50*j* is aligned with the coincident longitudinal central axes of the passages 40*j* and 246 to an orientation in which the longitudinal central axis of the anchor 50*j* extends generally perpendicular to the longitudinal central axis of the passages 40*j* and 246, i.e., the orientation shown in FIG. 13. To pivot the anchor 50*j* to the orientation shown in FIG. 13, as the anchor emerges from the outlet 84, the suture 38*j* is tensioned. The combination of the tension in the suture 38*j* and force applied against the trailing end 60*j* of the anchor 50*j* by the pusher member causes the anchor to pivot about the trailing end 60*j* of the anchor. The pusher member is then withdrawn and the suture 38*j* tensioned to move the anchor to the position shown in FIG. 13 in a manner similar to that described in the aforementioned U.S. Pat. Nos. 5,527,343 and 5,534,012.

Although it is believed that it may be preferred to change the orientation of the anchor 50*j* after it has emerged from the passages 40*j* and 246, the anchor could be blocked from reentering the passage in other ways if desired. Thus, the anchor could expand after emerging from the passages 40*j* and 246. This could be accomplished by having spring biased arms held in a retracted position by engagement of spring biased arms with the inner side surface of the tubular cylindrical member 240 which lines the passage 40*j*. Upon emerging from the passages 40*j* and 246, the arms would move outward under the influence of spring forces and extend radially outward beyond the edge of the exit from the passage 40*j*. If desired, the anchor 50*j* could be constructed so as to expand in a manner similar to that disclosed in U.S. Pat. No. 5,397,331 and/or U.S. Pat. No. 4,409,974.

Rather than expanding under the influence of stored energy, such as spring force, the anchor 50*j* could expand by absorbing body fluids. Thus, the anchor 50*j* may be compressed when it moves through the passages 40*j* and 246 and will expand and absorb body fluids after emerging from the passages 40*j* and 246. It is contemplated that the anchor 50*j* could be constructed so as to expand in any one of the ways disclosed in U.S. patent application Ser. No. 08/699,553 filed Aug. 19, 1996 by Peter M. Bonutti and entitled "Suture Anchor".

Once the anchor 50*j* has been moved through the passage 246, the passage is packed with bone particles and/or bone graft. The bone particles and/or bone graft contains bone growth inducing materials. In addition, the bone particles and/or bone graft may contain medicinal substances along with osteoinductive protein.

The limbs 72*j* and 74*j* of the suture 38*j* are then threaded through openings 64*j* and 66*j* in the second suture anchor 52*j*. The limbs 72*j* and 74*j* of the suture 38*j* are tensioned and the second anchor 52*j* is pressed against the outer side surface 250 of the bone 20*j*. While a predetermined tension force is maintained in the limbs 72*j* and 74*j* of the suture 38*j*, the knot 78*j* is tied in the suture to interconnect the two suture anchors 50*j* and 52*j* with the suture 38*j*. The suture 38*j* is then trimmed to the desired length.

Once the knot 78*j* has been tied between the limbs 72*j* and 74*j* of the suture 38*j*, the tension in the suture 38*j* presses the side surfaces 28*j* and 30 of the fracture 26*j* together. This pressure between the side surfaces 28 and 30*j* of the fracture 26*j* is maintained by the suture 38 and suture anchors 50*j* and 52*j* until the fracture heals. It is believed that it may be preferred to form the suture 38*j* and suture anchors 50*j* and 52*j* of a biodegradable material which, after the fracture 26*j* has healed, will dissolve in the patient's body.

The cylindrical tubular member 240 which is inserted into the passage 40*j* through the bone 20*j* performs the dual functions of lining the inside of the passage 40*j* and maintaining the two sections 22*j* and 24*j* of the bone in alignment. The cylindrical tubular member 240 could have a slot formed in a side wall of the tubular member to facilitate insertion of the tubular member into the passage 40*j*. It is contemplated that the cylindrical tubular member 240 could be left in the passage 40*j* after the bone securing assembly 32*j* has been installed. If the slotted or unslotted cylindrical tubular member 240 is to be left in the passage 40*j*, the cylindrical tubular member 240 may be formed of a biodegradable or bioerodible copolymer. When the cylindrical tubular member remains in the passage 40*j*, the suture 38*j* extends through the tubular member.

Although only a knot 78*j* has been shown in FIG. 13 adjacent to the second anchor 52*j*, a suture retainer could be provided to further hold the limbs 72*j* and 74*j* of the suture 38*j*. If a suture retainer is to be used in association with the knot 78*j*, the suture retainer will be moved along the limbs of the suture 38*j* toward the knot before the limbs 72*j* and 74*j* of the suture are trimmed to the short length shown in FIG. 13. The suture retainer would then be plastically deformed to grip the limbs 72*j* and 74*j* of the suture 38*j*. Thereafter, the suture limbs 72*j* and 74*j* would be trimmed to a desired length.

Although it is preferred to use a suture as the force transmitting member 38*j*, it should be understood that the anchors 50*j* and 52*j* could be interconnected by other force transmitting members, such as a rod formed of bone. Although the anchors 50*j* and 52*j* have constructions which enable them to be used with a suture, the anchors could be constructed so as to be used with other types of force transmitting members. For example, the anchors 50*j* and 52*j* could have thread convolutions to engage thread convolutions on a force transmitting member formed by a rod.

In the embodiment of the invention illustrated in FIG. 13, the member 240 is tubular. However, it is contemplated that a solid member could be used to transmit force to bone on opposite sides of the fracture 26*j*. Thus, the member 240 could be a solid cylindrical member formed of bone. The cylindrical member may be formed of freeze dried bone.

When the member 240 is a solid member, the suture or other force transmitting member 38*j* is eliminated. The solid member formed of bone becomes the force transmitting member. Anchors, corresponding to the anchors 50*j* and 52*j*, are connected to opposite ends of the solid member 240 formed of bone. The anchors may have internal thread convolutions which engage external thread convolutions on the solid member 240 formed of bone. Of course, other known connectors could be utilized to connect anchors with opposite ends of the solid member 240 formed of bone.

Nonlinear Suture Passage—Tubular Member

In the embodiment of the invention illustrated in FIG. 13, the passage 40*j* through which the suture 38*j* extends has a linear configuration. In the embodiment of the invention illustrated in FIG. 14, the passage through which the suture extends has a nonlinear configuration. Since the embodiment of the invention illustrated in FIG. 14 is generally similar to the embodiment of the invention illustrated in FIGS. 1—13, similar numerals will be utilized to identify similar components, the suffix letter "k" being associated with the components of the embodiment of the invention illustrated in FIG. 14 to avoid confusion.

A bone 20k as a fracture 26k which divides the bone into two sections 22k and 24k. Opposite side surfaces 28k and 30k of the fracture 26k are pressed together by a bone suture assembly 32k. The bone suture assembly 32k includes a suture 38k which extends between first and second suture anchors 50k and 52k.

The suture 38k is disposed in a passage 40k having a nonlinear configuration. Thus, the passage 40k includes a first section 140k which is skewed relative to a second section 142k of the passage 40k. A bend 144k is formed in the passage 40k at an intersection 146k of the first and second sections 140k and 142k of the passage 40k. The flexible suture 38k extends around the bend 144k along a nonlinear path between the suture anchors 50k and 52k. At the bend 144k, the suture 38k applies force against the section 24k of the bone 20k urging the section 24k toward the left (as viewed in FIG. 5). This force presses the sections 22k and 24k of the bone 20k firmly together at the fracture 26k.

The suture anchors 50k and 52k have the same cylindrical construction as the suture anchors 50, 52, 50j and 52j in the embodiment of the invention illustrated in FIGS. 2 and 13. A knot 78k (FIG. 14) is provided between limbs of the suture 38k to maintain a desired tension in the suture 38k. This tension pulls the suture anchors 50k and 52k toward each other. In addition, this tension presses the section 24k of the bone 20k firmly against the section 22k of the bone at the fracture 26k.

The first section 140k of the passage 40k is formed at an angle to and extends through a longitudinal central axis of the generally cylindrical bone 20k. The second section 142k of the passage 40k is formed in a direction perpendicular, i.e., along a radius, of the generally cylindrical bone 20k. The two sections 140k and 142k of the passage 40k terminate in the spongy cancellous bone tissue 44k.

When the suture assembly 32k is to be used to treat the fracture 26k in the bone 20k, the two sections 22k and 24k of the bone are pressed together at the fracture 26k to align the side surfaces 28k and 30k of the fracture. A drill or other hole forming apparatus is then used to form the first section 140k of the passage 40k. The drill or other hole forming apparatus is then used to form the second section 142k of the passage 40k. When the second section 142k of the passage 40k intersects the first section 140k of the passage 40k, formation of the section 142k of the passage 40k is interrupted.

Once the nonlinear passage 40k has been formed in the two sections 22k and 24k of the bone 20k, a tubular cylindrical liner 240k is inserted into the passage 40k. The tubular cylindrical liner 240k is formed by two separate cylindrical tubular members 252 and 254 which are inserted at opposite ends of the passage 40k. Alternatively, the tubular cylindrical liner 240k may be formed by a single flexible tubular member which is inserted into the section 140k of the passage 40k and then moved around the bend 144k into the section 142k of the passage 40k.

It is believed that it may be preferred to form the tubular members 252 and 254 of bone. The bone forming the tubular members 252 and 254 may be either human or animal bone. The tubular members 252 and 254 may be formed of freeze dried human bone.

The leading end 242k of the tubular member 252 is disposed in the compact outer layer 42k of the bone 20k. Similarly, the trailing end 244k of the tubular member 254 is disposed in the compact outer layer 42k of the bone 20k. The tubular member 252 extends across the fracture 26k and stabilizes the two sections 22k and 24k of the bone 20k. Since the end portions 242k and 244k of the tubular members 252 and 254 are disposed in the compact outer layer 42k of the bone 20k, the tubular members are solidly supported and hold the two sections 22k and 24k of the bone 20k in alignment at the fracture 26k.

The opposite ends 242k and 244k of the tubular members 252 and 254 are axially spaced from a generally cylindrical outer side surface 250k on the bone 20k. This enables the anchors 50k and 52k to be pressed against the outer side surface 250k of the bone 20k. Therefore, tension forces in the suture 38k are transmitted through the anchors 50k and 52k to the bone 20k.

The cylindrical anchor 50k, with the suture 38k connected thereto, is then positioned in axial alignment with the section 142k of the passage 40k. The leading end 58k of the anchor 50k is then moved into the section 142k of the passage 40k lined by the tubular member 254. A flexible pusher member applies force against the trailing end 60k of the anchor 50k and pushes the anchor around the bend 144k and through the section 140k of the passage 40k lined by the tubular member 252.

Alternatively, a flexible wire or other member could be inserted into the section 140k of the passage 40k. The wire would move around the bend 144k and extend outward from the section 142k of the passage. The wire would then be connected with the anchor 50k and suture 38k. The leading end 58k of the anchor 50k would then be inserted into the section 142k of the passage 40k. Tension on the wire would pull the anchor 50k around the bend 144k and out of the section 140k of the passage 40k.

The passages in the tubular members 252 and 254 may be packed with bone particles and/or bone graft. Bone osteoinductive protein (BMP) may be provided in the tubular members. Antibiotics and/or other medicants may be included along with collagen.

The suture 38k is then threaded through openings in the suture anchor 52k. The suture 38k is then tensioned and the second anchor 52k is pressed against the outer side surface of the bone 20k. While a predetermined tension force is maintained in the suture 38k, the knot 78k is tied.

In the illustrated embodiment of the invention, the two sections 140k and 142k of the passage 40k have a straight cylindrical configuration. However, it is contemplated that the sections 140k and 142k of the passage 40k could have a different configuration if desired. For example, the section 140k and/or 142k of the passage 40k could have a nonlinear central axis and could have a noncircular cross-sectional configuration of desired.

Body tissue, corresponding to the body tissue 132 of FIG. 4 could be disposed between the anchor 50k and/or 52k and the bone 20k. Although the suture 38k has been illustrated as having a pair of limbs or sections which extend between the anchors 50k and 52k, the suture 38k could have a single limb or section if desired. The anchor 50c could mechanically expand, by absorbing body liquid or under the influence of expansion springs, after the anchor has emerged from the passage 40k to prevent the anchor from being pulled back through the passage.

Retainer and Tubular Member

In the embodiment of the invention illustrated in FIG. 13, a pair of suture anchors 50j and 52j are connected with the suture 38j to maintain tension in the suture and pressure against opposite side surfaces 28j and 30j of the fracture 26j. In the embodiment of the invention illustrated in FIG. 15, a suture retainer is used in place of one of the suture anchors. Since the embodiment of the invention illustrated in FIG. 15 is generally similar to the embodiment of the invention illustrated in FIG. 13, similar numerals will be utilized to designate similar components, the suffix letter "m" being associated with the embodiment of the invention illustrated in FIG. 15 to avoid confusion.

A bone 20m has sections 22m and 24m which are separated by a fracture 26m. The fracture 26m has side surfaces 28m and 30m which are pressed together by a bone suture assembly 32m. A suture 38m extends through a cylindrical passage 40m which extends diametrically through the generally cylindrical bone 20m. The suture 38m has a pair of limbs or sections 72m and 74m which are connected with a suture anchor 50m. The suture anchor 50m has the same construction as the suture anchor 50 of FIG. 2.

Once the passage 40 has been formed in the two tubular sections 22m and 24m of the bone 20m, a tubular cylindrical member 240m is installed into the passage 40m and extends diametrically through the bone 20m. The leading end 242m of the cylindrical member 240m is aligned with a circular outlet 84m from the passage 40m. The opposite or trailing end 244m of the tubular member 240m is aligned with a circular inlet 86m to the passage 40m.

The tubular member 240m has a thin cylindrical wall which engages the sections 22m and 24m of the bone 20m. A cylindrical inner side surface of the tubular member 240m defines a cylindrical passage 246m having a diameter which is only slightly less than the diameter of the passage 40m. The tubular member 240m is formed of bone. Alternatively, the tubular member 240m could be formed of a biodegradable material.

The leading end 242m of the tubular member 240m is disposed in the compact outer layer 42m of the bone 20m. Similarly, the trailing end 244m of the tubular member 240m is disposed in the compact outer layer 42m of the bone 20m. The tubular member 240m extends across the fracture 26m and stabilizes the two sections 22m and 24m of the bone 20m. Since the opposite end portions of the tubular member 240m are disposed in the compact outer layer 42m of the bone 20m, the tubular member is solidly supported and holds the two sections 22m and 24m of the bone 20m in alignment at the fracture 26m.

The opposite ends 242m and 244m of the tubular member 240m are axially spaced from a generally cylindrical outer side surface 250m on the bone 20m. This enables the anchors 50m and 92m to be pressed against the outer side surface 250m of the bone 20m. Therefore, tension forces in the suture 38m are transmitted through the anchors 50m and 92m to the bone 20m.

The tubular member 240m is formed of freeze dried human bone. The tubular member 240m is packed with bone and/or bone graft. The tubular member 240m also contains bone osteoinductive protein (BMP). Suitable medicants may be provided in the tubular member 240m.

A suture retainer 92m is used in place of the suture anchor 52 of FIG. 2. The suture retainer 92m (FIG. 15) has a spherical configuration. A cylindrical passage 94m extends through the center of the spherical suture retainer 92m. The sections 72m and 74m of the suture 38m extend around the spherical outer side surface of the suture retainer 92m. Thus, a loop is formed in each of the sections 72m and 74m around portions of the suture retainer 92m.

If desired, the suture retainer 92m could have a different configuration. For example, the suture retainer 92m could have an oval or elliptical configuration. Although the passage 94m has a linear central axis, the passage could have a nonlinear central axis. If desired, a plurality of passages having the same or different configurations could be provided in the suture retainer 92m.

After the suture 38m has been inserted through the suture retainer 92m, the suture retainer 92m is moved along the sections 72m and 74m of the suture 38m toward the bone 20m. The suture retainer 92m is formed as one piece of a polymeric material having a relatively low coefficient friction. Therefore, the two sections 72m and 74m of the suture 30m can readily slide along the surfaces of the suture retainer 52m while the suture retainer moves toward the bone 20m.

A predetermined tension is maintained in the sections 72m and 74m of the suture 38m while the suture retainer 92m is pressed against the bone 20m. This results in the suture 38m being pulled tightly against the suture anchor 50m. The tension in the suture 38m is effective to press the suture anchor 50m and retainer 92m against opposite sides of the bone 20m with a predetermined force.

While the sections 72m and 74m of the suture 38m are being tensioned with a predetermined force, the suture retainer 92m is plastically deformed in the same manner as previously described in conjunction with the embodiment of the invention illustrated in FIG. 3. To plastically deform the suture retainer 92m, a plurality of force applying or clamp members are pressed against the suture retainer with a predetermined minimum force. The force applied against the suture retainer 92m by the force applying members is sufficient to cause plastic deformation of the material of the suture retainer.

The force is applied against the suture retainer 92m while the suture retainer is at a temperature which is below the transition temperature of the biodegradable polymer which forms the suture retainer 92m. Thus, the suture retainer 92m is at approximately the same temperature as the bone 20m when the force is applied against the suture retainer. The force causes the material of the suture retainer 92m to flow and grip the sections 72m and 74m of the suture 38m.

The suture retainer 92m may be formed of many different materials. However, it is believed that it will be preferred to form the suture retainer 92m of a biodegradable polymer. One biodegradable polymer which may be utilized is polycaperlactone. Alternatively, the suture retainer 92m could be formed of polyethylene oxide terephthalate or polybutylene terephthalate. It is also contemplated that other biodegradable or bioerodible copolymers could be utilized.

Although it is preferred to form the suture retainer 92m of a biodegradable material, the suture retainer could be formed of a material which is not biodegradable. For example, the suture retainer 92m could be formed of an acetyl resin, such as "DELRIN" (trademark). Alternatively, the suture retainer 92m could be formed of para-dimethylamino-benzenediazo sodium sulfonate, such as "DEXON" (trademark). The construction of the suture retainer 92m and the manner in which is cooperates with the suture 38m is the same as is disclosed in U.S. patent application Ser. No. 08/905,084 filed Aug. 1, 1997 by Peter M. Bonutti et al. and entitled "Method and Apparatus for Securing a Suture".

The suture retainer 92m is plastically deformed to grip the limbs 72m and 74m of the suture 38m. However, the suture retainer 92m could be constructed so as to be mechanically actuated to grip the suture 38m. If desired, a combination of a mechanical gripping action and plastic deformation could be utilized by a retainer to grip the suture 38m.

Conclusion

In view of the foregoing description, it is apparent that the present invention relates to a method of securing sections 22 and 24 of a fractured bone 20. Sections 22 and 24 of a fractured bone 20 are held against movement relative to each other by a force transmitting member, such as a suture 38, which extends through a passage 40 in the bone. The passage 40 in the bone may have a linear or nonlinear configuration. Tension is maintained in the force transmitting member 38 to press surfaces 28 and 30 on the fracture together by securing anchors 50 and 52 or suture retainers 92 to opposite ends of the force transmitting member 38. It is believed that a suture 38 may advantageously be used as the force transmitting member.

A tubular member 240 is positioned in a linear passage (FIGS. 13 and 15) or a nonlinear passage (FIG. 14) through the bone 20. The tubular member 240 extends into portions of the passage 40 on opposite sides of the fracture 26. End portions of the tubular member may be positioned in a compact outer layer 42 of the bone. The tubular member 240 may be formed of bone. The force transmitting member 38 may be formed of bone or other body tissue.

Having described the invention, the following is claimed:

1. A method of treating a fractured bone, said method comprising the steps of forming a passage extending through bone on opposite sides of the fracture, positioning a tubular member in the passage with the tubular member extending into portions of the passage on opposite sides of the fracture, positioning a suture in the tubular member, positioning first and second anchors adjacent to bone on opposite sides or the fracture with the anchors and suture interconnected, and transmitting force through the suture to the first and second anchors to urge bone on opposite sides of the fracture together while at least a portion of the suture is disposed in the tubular member.

2. A method as set forth in claim 1 wherein said step of positioning first and second anchors in engagement with bone on opposite sides of the fracture with the anchors and suture interconnected includes moving the first anchor through the tubular member while the first anchor is connected with the suture.

3. A method as set forth in claim 2 wherein said step of positioning first and second anchors adjacent to bone on opposite sides of the fracture with the anchors and suture interconnected includes connecting the second anchor with the suture after performing said step of moving the first anchor through the tubular member.

4. A method as set forth in claim 1 wherein said step of positioning first and second anchors adjacent to bone on opposite sides of the fracture with the anchors and suture interconnected includes moving the first anchor through the tubular member with the first anchor in a first orientation, and changing the orientation of the first anchor from the first orientation to a second orientation after having performed said step of moving the first anchor through the tubular member, said steps of moving the first anchor through the tubular member and changing the orientation of the first anchor being performed with the suture connected with the first anchor.

5. A method as set forth in claim 1 wherein said step of positioning first and second anchors adjacent to bone on opposite sides of the fracture with the anchors and suture interconnected includes securing the suture relative to the second anchor by tying a knot in the suture.

6. A method as set forth in claim 1 wherein said step of positioning first and second anchors adjacent to bone on opposite sides of the fracture with the anchors and suture interconnected includes deforming a suture retainer to grip the suture with the suture retainer.

7. A method as set forth in claim 1 wherein said step of positioning a tubular member in the passage includes positioning the tubular member in the passage with a first end of the tubular member disposed adjacent to and spaced apart from an outer side surface of the bone on a first side of the fracture, with a second end of the tubular member disposed adjacent to and spaced apart from an outer side surface of the bone disposed on a second side of the fracture, and with a portion of the tubular member disposed between the first and second ends of the tubular member extending across the fracture.

8. A method as set forth in claim 1 wherein said step of positioning a tubular member in the passage includes positioning the tubular member in the passage with a first end portion of the tubular member disposed in engagement with a compact outer layer of the bone on a first side of the fracture and with a second end portion of the tubular member disposed in engagement with a compact outer layer of the bone on a second side of the fracture.

9. A method as set forth in claim 1 further including the step of packing the tubular member with bone particles.

10. A method as set forth in claim 1 wherein said step of positioning a tubular member in the passage includes positioning a tubular member formed of bone in the passage.

11. A method as set forth in claim 10 further including the step of packing the passage in the tubular member formed of bone with bone osteoinductive protein.

12. A method of treating a fractured bone, said method comprising the steps of forming a passage extending through bone on opposite sides of the fracture, positioning a tubular member in the passage, positioning a suture in the passage with a portion of the suture extending through the tubular member and with a portion of the suture connected with an anchor disposed adjacent to a first end of the passage, tensioning the suture to transmit force from the suture to the anchor, gripping a portion of the suture with a retainer disposed adjacent to a second end of the passage, and transmitting force through the suture to the anchor and retainer to urge opposite sides of the fracture together while at least a portion of the suture is disposed in the tubular member.

13. A method as set forth in claim 12 wherein said step of gripping the suture with the retainer includes deforming material of the suture retainer.

14. A method as set forth in claim 12 further including the step of moving the retainer along the suture into engagement with the bone with the suture retainer spaced from the tubular member, said step of transmitting force through the suture to the anchor and retainer includes pressing the retainer against the bone on a side of the fracture.

15. A method as set forth in claim 12 wherein said step of positioning the suture in the passage with a portion of the suture extending through the tubular member includes moving the anchor through the tubular member while the anchor is connected with the suture.

16. A method as set forth in claim 12 further including the step of changing the orientation of the anchor relative to the tubular member after having performed said step of moving the anchor through the tubular member.

17. A method as set forth in claim 12 wherein said step of positioning a tubular member in the passage includes positioning the tubular member in the passage with a first end of the tubular member disposed adjacent to and spaced apart from an outer side surface of the bone disposed on a first side of the fracture, with a second end of the tubular member disposed adjacent to and spaced apart from an outer side surface of the bone disposed on a second side of the fracture, and with a portion of the tubular member disposed between the first and second ends of the tubular member extending across the fracture.

18. A method as set forth in claim 12 wherein said step of positioning a tubular member in the passage includes positioning the tubular member in the passage with a first end portion of the tubular member disposed in engagement with a compact outer layer of the bone on a first side of the fracture and with a second end portion of the tubular member disposed in engagement with the compact outer layer of the bone on a second side of the fracture.

19. A method as set forth in claim 12 further including the step of packing the tubular member with bone particles.

20. A method as set forth in claim 12 wherein said step of positioning a tubular member in the passage includes positioning a tubular member formed of bone in the passage.

21. A method as set forth in claim 20 further including the step of packing the passage in the tubular member formed of bone with bone osteoinductive protein.

22. A method of treating a fractured bone, said method comprising the steps of forming a nonlinear passage which extends across the fracture from bone on a first side of the fracture to bone on a second side of the fracture, positioning a tubular member in the nonlinear passage with the tubular member extending across the fracture, positioning anchors adjacent to opposite ends of the nonlinear passage with a suture extending between the anchors and through the tubular member, and transmitting force through the suture to the anchors to urge the bone on opposite sides of the fracture together while at least a portion of the suture is disposed in the tubular member.

23. A method as set forth in claim 22 wherein said step of positioning anchors adjacent to opposite ends of the nonlinear passage with a suture extending between the anchors and through the tubular member includes moving an anchor connected with the suture through the nonlinear passage.

24. A method as set forth in claim 22 further including the step of packing the tubular member with bone particles.

25. A method as set forth in claim 22 wherein said step of positioning a tubular member in the passage includes positioning a tubular member formed of bone in the passage.

26. A method as set forth in claim 25 further including the step of packing the passage in the tubular member formed of bone with bone osteoinductive protein.

27. A method of treating a fractured bone having a compact outer layer which encloses cancellous bone, said method comprising the steps of forming a passage which extends through the compact outer layer on a portion of the bone disposed on a first side of the fracture, through the cancellous bone on opposite sides of the fracture, and through the compact outer layer on a portion of the bone on a second side of the fracture, positioning a tubular member in the passage with a first end portion of the tubular member in engagement with the compact outer layer on the portion of the bone on the first side of the fracture, with a second end portion of the tubular member in engagement with the compact outer layer on the portion of the bone on the second side of the fracture, and with a portion of the tubular member disposed between the first and second end portions of the tubular member in engagement with the cancellous bone on opposite sides of the fracture, positioning anchors adjacent to opposite ends of the passage with a suture extending between the anchors and through the tubular member, and transmitting force through the suture to the anchors to urge the portions of the bone on the first and second sides of the fracture toward each other while at least a portion of the suture is disposed in the tubular member.

28. A method as set forth in claim 27 wherein said step of positioning anchors adjacent to opposite ends of the passage with the suture extending between the anchors and through the tubular member includes moving one of the anchors through the tubular member while the one anchor is connected with the suture.

29. A method as set forth in claim 27 wherein said step of positioning tubular member in the passage includes positioning the tubular member in the passage with the first end portion of the tubular member spaced apart from an outer side surface of the compact outer layer on the portion of the bone on the first side of the fracture and with the second end portion of the tubular member spaced apart from an outer side surface of the compact outer layer on the portion of the bone on the second side of the fracture.

30. A method as set forth in claim 27 wherein said step of positioning anchors adjacent opposite ends of the passage with the suture extending between the anchors and through the tubular member includes moving one of the anchors in the tubular member with the one anchor in a first orientation and with the suture connected with the one anchor in a first orientation and with the suture connected with the one anchor, moving the one anchor out of the tubular member, and changing the orientation of the one anchor from the first orientation to a second orientation, said step of transmitting force through the suture to the anchors being performed wit the one anchor in the second orientation.

31. A method as set forth in claim 27 further including the step of packing the tubular member with bone particles.

32. A method as set forth in claim 27 wherein said step of positioning a tubular member in the passage includes positioning a tubular member formed of bone in the passage.

33. A method as set forth in claim 32 further including the step of packing the passage in the tubular member formed of bone with bone osteoinductive protein.

34. A Method of treating a fractured bone, said method comprising the steps of forming a passage extending through bone on opposite sides of the fracture, positioning a tubular member in the passage with the tubular member extending into portions of the passage on opposite sides of the fracture, positioning a force transmitting member in the tubular member, positioning first and second anchors adjacent to bone on opposite sides or the fracture with the anchors and force transmitting member interconnected, and transmitting force through the force transmitting member to the first and second anchors to urge bone on opposite sides of the fracture together while at least a portion of the force transmitting member is disposed in the tubular member.

35. A method as set forth in claim 34 wherein said step of positioning first and second anchors in engagement with bone on opposite sides of the fracture with the anchors and force transmitting member interconnected includes moving the first anchor through the tubular member while the first anchor is connected with the force transmitting member.

36. A method as set forth in claim 35 wherein said step of positioning first and second anchors adjacent to bone on opposite sides of the fracture with the anchors and force transmitting member interconnected includes connecting the second anchor with the force transmitting member after performing said step of moving the first anchor through the tubular member.

37. A method as set forth in claim 34 wherein said step of positioning first and second anchors adjacent to bone on opposite sides of the fracture with the anchors and force transmitting member interconnected includes moving the first anchor through the tubular member with the first anchor in a first orientation, and changing the orientation of the first anchor from the first orientation to a second orientation after having performed said step of moving the first anchor through the tubular member, said steps of moving the first anchor through the tubular member and changing the orientation of the first anchor being performed with the force transmitting member connected with the first anchor.

38. A method as set forth in claim 34 wherein the force transmitting member is a suture and said step of positioning first and second anchors adjacent to bone on opposite sides of the fracture with the anchors and force transmitting member interconnected includes securing the suture relative to the second anchor by tying a knot in the suture.

39. A method as set forth in claim 34 wherein the force transmitting member is a suture and said step of positioning first and second anchors adjacent to bone on opposite sides of the fracture with the anchors and force transmitting member interconnected includes deforming a suture retainer to grip the suture with the suture retainer.

40. A method as set forth in claim 34 wherein said step of positioning a tubular member in the passage includes positioning the tubular member in the passage with a first end of the tubular member disposed adjacent to and spaced apart from an outer side surface of the bone on a first side of the fracture, with a second end of the tubular member disposed adjacent to and spaced apart from an outer side surface of the bone disposed on a second side of the fracture, and with a portion of the tubular member disposed between the first and second ends of the tubular member extending across the fracture.

41. A method as set forth in claim 34 wherein said step of positioning a tubular member in the passage includes positioning the tubular member in the passage with a first end portion of the tubular member disposed in engagement with a compact outer layer of the bone on a first side of the fracture and with a second end portion of the tubular member disposed in engagement with a compact outer layer of the bone on a second side of the fracture.

42. A method as set forth in claim 34 further including the step of packing the tubular member with bone particles.

43. A method as set forth in claim 34 wherein said step of positioning a tubular member in the passage includes positioning a tubular member formed of bone in the passage.

44. A method as set forth in claim 43 further including the step of packing the passage in the tubular member formed of bone with bone osteoinductive protein.

45. A Method of treating a fractured bone, said method comprising the steps of forming a passage extending through bone on opposite sides of the fracture, positioning a tubular member formed of bone in the passage with the tubular member formed of bone extending into portions of the passage on opposite sides of the fracture, and placing bone growth inducing materials in the tubular member formed of bone.

46. A method as set forth in claim 45 wherein said step of placing bone growth inducing materials in the tubular member formed of bone includes placing bone particles in the tubular member formed of bone.

47. A method as set forth in claim 45 wherein said step of placing bone growth inducing materials in the tubular member formed of bone includes placing bone graft in the tubular member.

48. A method as set forth in claim 45 wherein said step of placing bone growth inducing materials in the tubular member formed of bone includes placing osteoinductive protein in the tubular member formed of bone.

49. A method as set forth in claim 45 wherein said step of placing bone growth inducing materials in the tubular member formed of bone is performed after performing said step of positioning the tubular member formed of bone in the passage.

50. A method as set forth in claim 45 further including the steps of positioning a force transmitting member in the tubular member and transmitting force through the force transmitting member to bone on opposite sides of the fracture.

51. A method as set forth in claim 50 further including the step of positioning anchors adjacent to opposite ends of the tubular member and transmitting force through the force transmitting member to the anchors.

52. A method as set forth in claim 50 wherein said step of positioning a force transmitting member in the tubular member includes positioning a force transmitting member formed of bone in the tubular member.

53. A method as set forth in claim 45 wherein said step of positioning a tubular member formed of bone in the passage includes positioning a tubular member formed of freeze dried bone in the passage.

54. A Method of treating a fractured bone, said method comprising the steps of forming a passage extending through bone on opposite sides of the fracture, positioning a member formed of bone in the passage with the member formed of bone extending into portions of the passage on opposite sides of the fracture, and transmitting force through the member formed of bone to bone on opposite sides of the fracture to urge bone on opposite sides of the fracture together.

55. A method as set forth in claim 54 further including the steps of connecting a first anchor with a first end portion of the member formed of bone, and connecting a second anchor with a second end portion of the member formed of bone.

56. A method as set forth in claim 54 wherein said member formed of bone has a tubular configuration, said method further includes the steps of positioning a force transmitting member in the member formed of bone, said step of transmitting force through the member formed of bone to bone on opposite sides of the fracture includes transmitting force through the force transmitting member while the force transmitting member is at least partially enclosed by the member formed of bone.

* * * * *

UNITED STATES PATENT AND TRADEMARK OFFICE
CERTIFICATE OF CORRECTION

PATENT NO. : 6,045,551
DATED : April 4, 2000
INVENTOR(S) : Peter M. Bonutti

It is certified that error appears in the above-indentified patent and that said Letters Patent is hereby corrected as shown below:

Column 29, line 26, change "or " to "of"

Column 32, line 23 change "wit" to "with"

Column 32 line 33, change "Method" to "method"

Column 33, line 43, change "Method" to "method"

Column 34, line 31, change "Method" to "method"

Signed and Sealed this

First Day of May, 2001

Attest:

NICHOLAS P. GODICI

*Attesting Officer*      *Acting Director of the United States Patent and Trademark Office*